United States Patent [19]

Bowman et al.

[11] Patent Number: 5,764,034
[45] Date of Patent: Jun. 9, 1998

[54] BATTERY GAUGE FOR A BATTERY OPERATED INFUSION PUMP

[75] Inventors: George Bowman, Vernon Hills; Grace Esche, Algonquin, both of Ill.

[73] Assignee: Baxter International Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 630,359

[22] Filed: Apr. 10, 1996

[51] Int. Cl.⁶ .................. H42J 7/04; A61M 31/00
[52] U.S. Cl. .................. 320/155; 320/DIG. 21; 340/636; 604/65; 324/427
[58] Field of Search .................. 320/2, 21, 39, 320/155, 156, 3, 22, 40, DIG. 13, DIG. 21; 324/429–450; 340/635, 636; 604/67, 152; 128/DIG. 12

[56] References Cited

U.S. PATENT DOCUMENTS

| 3,886,442 | 5/1975 | Chiku et al. ............... 324/29.5 |
| 4,094,318 | 6/1978 | Burke et al. ............... 128/214 E |
| 4,377,787 | 3/1983 | Kikuoka et al. ............ 324/431 |
| 4,390,841 | 6/1983 | Martin et al. ............. 324/427 |
| 4,457,750 | 7/1984 | Hill ....................... 604/65 |
| 4,553,958 | 11/1985 | LeCocq .................... 604/67 |
| 4,558,281 | 12/1985 | Codd et al. ............... 324/433 |
| 4,595,880 | 6/1986 | Patil ...................... 324/427 |
| 4,619,653 | 10/1986 | Fischell .................. 604/891 |
| 4,949,046 | 8/1990 | Seyfang ................... 324/427 |
| 5,317,269 | 5/1994 | Mills et al. .............. 324/427 |
| 5,321,392 | 6/1994 | Skakoon et al. ........... 340/363 |
| 5,321,627 | 6/1994 | Reher ..................... 364/483 |
| 5,394,089 | 2/1995 | Clegg ..................... 324/427 |
| 5,423,747 | 6/1995 | Amano .................... 604/65 |
| 5,451,881 | 9/1995 | Finger .................... 324/433 |
| 5,459,671 | 10/1995 | Duley ..................... 364/483 |
| 5,464,391 | 11/1995 | Epstein et al. ........... 604/67 |
| 5,541,489 | 7/1996 | Dunstan ................... 320/134 |
| 5,570,025 | 10/1996 | Lauritsen et al. .......... 324/433 |
| 5,600,230 | 2/1997 | Dunstan ................... 340/636 |
| 5,652,502 | 7/1997 | Van Phouc et al. .......... 320/30 |
| 5,661,463 | 8/1997 | Letchak et al. ............ 340/636 |
| 5,691,742 | 11/1997 | O'Connor et al. ........... 345/116 |

FOREIGN PATENT DOCUMENTS

| 0-408-483 | 7/1990 | European Pat. Off. ....... A61M 5/172 |
| 0-496-537 | 1/1992 | European Pat. Off. ....... G01R 31/36 |
| 0-637-754 | 1/1994 | European Pat. Off. ....... G01R 31/36 |
| 2063290 | 6/1971 | Germany . |
| 0211674 | 12/1983 | Japan ..................... G01R 31/36 |
| 0250774 | 10/1989 | Japan ..................... G01R 31/36 |
| 406281709 A | 10/1994 | Japan ..................... G01R 31/36 |
| 1-062-831 | 2/1965 | United Kingdom . |
| 2-121-971 | 6/1983 | United Kingdom ........... G01R 31/36 |
| 2-221-046 | 7/1989 | United Kingdom ........... G01R 31/36 |
| 2-278-452 | 5/1994 | United Kingdom ........... G01R 31/36 |
| 2-283-331 | 10/1994 | United Kingdom ........... G01R 31/36 |
| WO 86/00418 | 1/1986 | WIPO ..................... G01R 31/36 |
| WO 8901169 | 2/1989 | WIPO ..................... G01R 31/36 |

OTHER PUBLICATIONS

"Instrumentation for a Wearable Artificial Kidney", Medical & Biological Engineering & Computing, pp. 75–77, Jan. 1977.

Primary Examiner—Peter S. Wong
Assistant Examiner—Gregory J. Toatley, Jr.
Attorney, Agent, or Firm—P. E. Schaafsma; F. C. Kowalik

[57] ABSTRACT

The present invention provides an estimate of the amount of time left on the battery by monitoring not only the voltage available from the battery, but also the amount of current flowing from the battery. It has been found that periodic sampling of the battery voltage and current drain enables accurate battery monitoring. The sampling technique alternates between sampling battery voltage and sampling current drain. An electric circuit is provided which enables the cost-effective sampling to occur. A method is then applied to the sampling signals by a microprocessor which determines the amount of time left under battery power. In a preferred embodiment, a graphic representation is provided of the amount of battery time left.

15 Claims, 18 Drawing Sheets

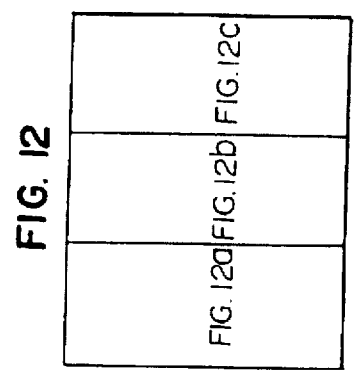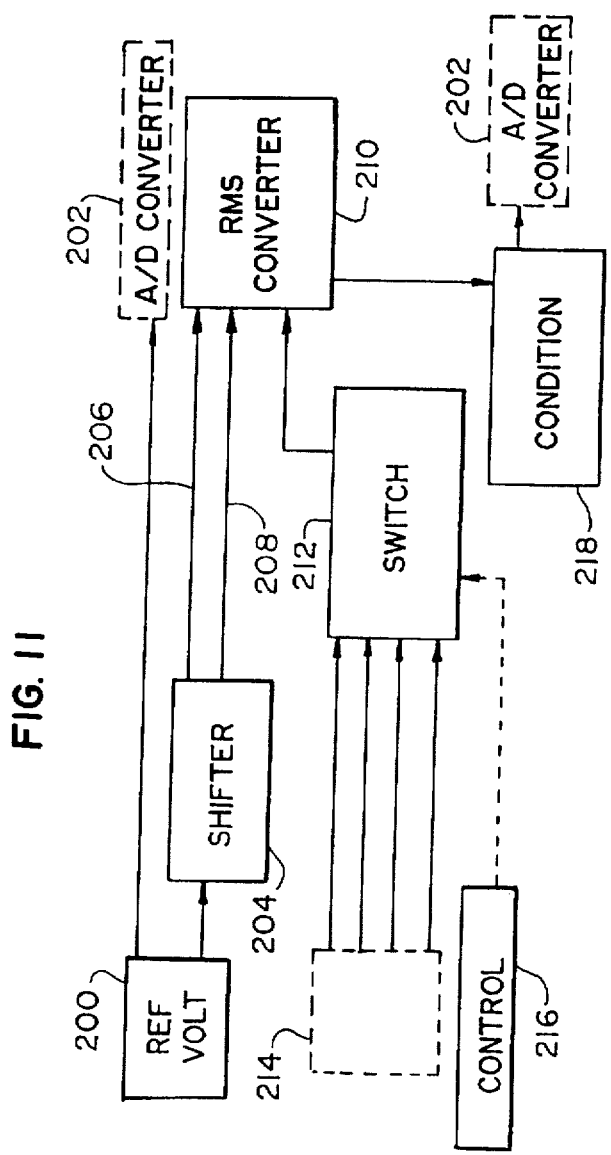

BATTERY GAUGE FOR A BATTERY OPERATED INFUSION PUMP

FIELD OF THE INVENTION

The present invention relates to battery gauges in general and in particular to medical infusion pump battery gauges.

BACKGROUND OF THE INVENTION

The administration of intravenous medical fluids to a patient is well known in the art. Typically, a solution such as saline, glucose or electrolyte contained in a glass or flexible container is fed to a patient's venous system through a conduit such as a polyvinyl chloride (PVC) intravenous (IV) tube which is accessed to the patient by a catheter. Many times, the fluid is infused under the forces of gravity, and the rate of flow is controlled by a roller clamp which is adjusted to restrict the flow lumen of the IV tube until the desired flow rate is obtained.

Flow from the container to the patient also is known to be regulated by means other than a roller clamp. It is becoming more and more common to use an electronically controlled infusion pump. Such pumps include, for example, peristaltic-type pumps and valve-type pumps. Peristaltic-type pumps typically include an array of cams angularly spaced from each other which drive cam followers connected to pressure fingers. These elements cooperate to impart a linear wave motion on the pressure fingers. This linear wave motion is used to apply force to the IV tube, which imparts the motion to the fluid in the IV tube thereby propelling the fluid. An alternative type of peristaltic pump employs a plurality of roller members which roll over the IV tube to impart the motion to the fluid in the IV tube. Medical infusion pumps also employ pumping chambers having upstream and downstream valves to sequentially impart the propulsion to the fluid. Such valve-type pumps typically require the use of a specialized pumping cassette chamber, which is contained on a dedicated IV tube between the patient and the source of fluid.

All of these medical infusion pumps must be capable of maintaining the pumping activity not only when powered from the alternating current (AC) supplied in the facility wall outlets, but also when on auxiliary direct current (DC) battery power. This is because patients to whom medical fluids are being administered must often be moved, even when admitted to hospital facilities. For example, if a patient requires remote testing procedures while being administered by an infusion pump, the infusion pump will be unplugged from the wall outlet so the patient can be transported to the testing area. During this transportation and remote testing, the infusion pump operates off the auxiliary battery power.

One issue which use of the auxiliary battery power raises is the monitoring of the available power in the battery at any given time. It is clearly important for the health care provider to know that sufficient power is available for the amount of time the patient will be ambulatory. While pumps have included battery monitoring capabilities in the past, such monitoring capabilities only measured the available voltage from the battery. When the voltage decreased to below a predetermined value, a battery low alert was sounded. When the voltage decreased below a predetermined critical value, a battery alarm sounded. However, because the monitoring was not that accurate, such alert and alarm levels were set conservatively, which often gave rise to alert or alarm conditions even when the pump had sufficient power for the required time. While more sensitive monitoring was available, such increased sensitivity was not cost effective, often costing more than the infusion pump itself.

What is needed is a medical infusion pump which incorporates cost-effective, sensitive battery monitoring. It would be further advantageous for an infusion pump to be capable of providing an accurate estimate of the amount of time left on auxiliary battery power to the health care provider. It would be further advantageous to provide a battery monitor capable of such cost-effective, sensitive battery monitoring in environments similar to battery monitoring in medical infusion pumps.

SUMMARY OF THE INVENTION

The present invention provides a medical infusion pump which incorporates cost-effective, sensitive battery monitoring. The present invention provides an infusion pump which is capable of providing an accurate estimate of the amount of time left on battery power to the health care provider. The present invention provides a battery monitor capable of such cost-effective, sensitive battery monitoring in environments similar to battery monitoring in infusion pumps.

The present invention provides an estimate of the amount of time left on the battery by monitoring not only the voltage available from the battery, but also the amount of current flowing from the battery. It has been found that periodic sampling of the battery voltage and current drain enables accurate battery monitoring. The sampling technique alternates between sampling battery voltage and sampling current drain. An electric circuit is provided which enables the cost-effective sampling to occur. A method is then applied to the sampling signals by a microprocessor which determines the amount of time left under battery power. In a preferred embodiment, a graphic representation is provided of the amount of battery time left.

BRIEF DESCRIPTION OF THE DRAWINGS

FIG. 11 is a block diagram of a battery gauge circuit constructed in accordance with the principles of the present invention;

DETAILED DESCRIPTION OF A PREFERRED EMBODIMENT

Figure 1:
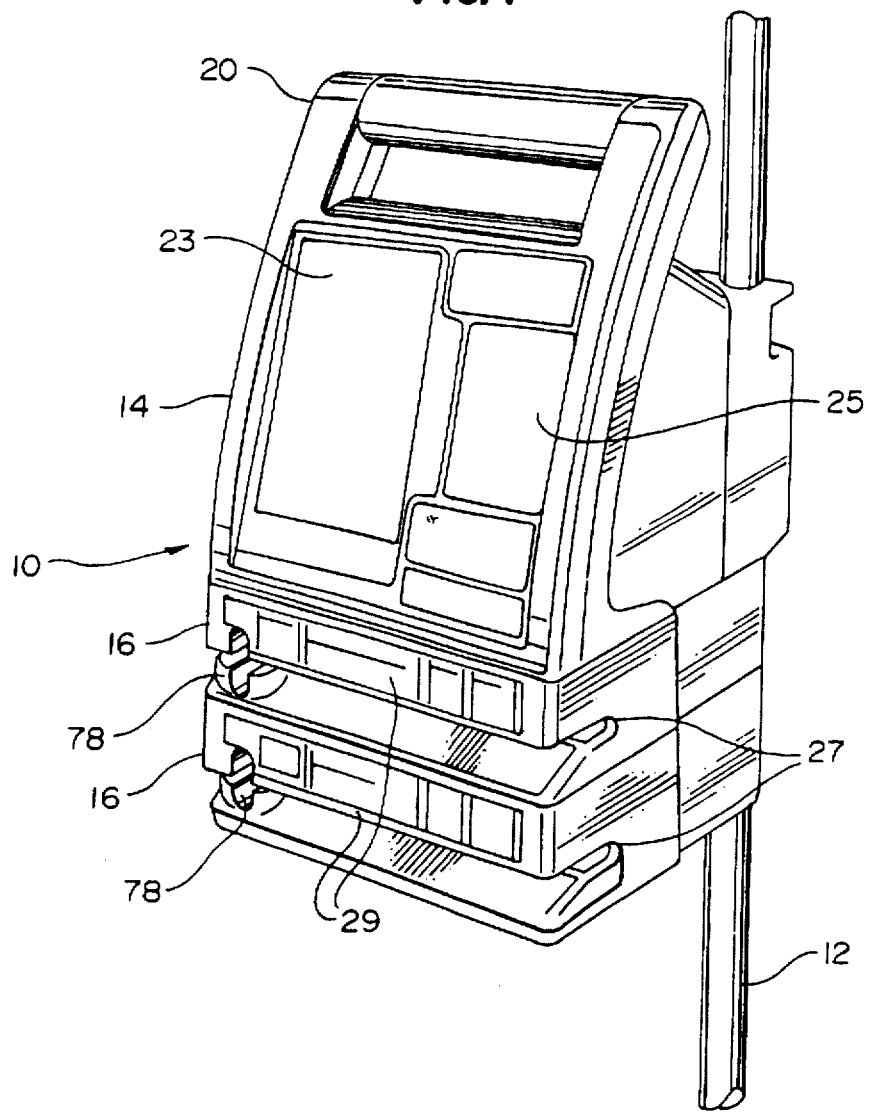
FIG. 1 is a perspective view of an infusion pump.
Figure 2:
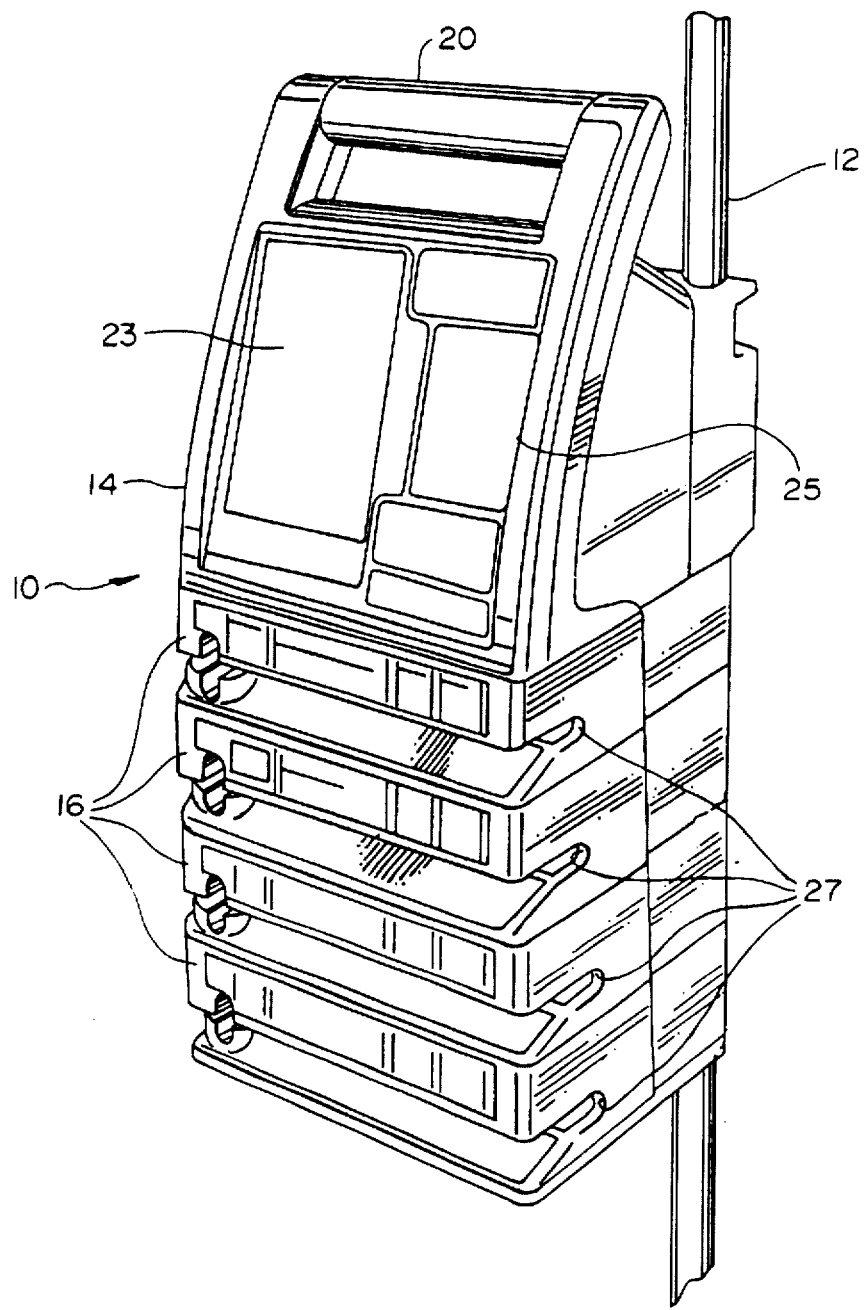
FIG. 2 is a perspective view of an alternative infusion pump.

Referring to FIG. 1, an intravenous fluid infusion pump is referred to generally as 10. The pump 10 is clamped onto a standard IV pole 12. The IV pole 12 typically includes at its lower periphery wheels which allow the IV pole, pump and any additional medical devices supported thereon some level of mobility so the patient can be moved. The pump 10 includes a main body portion 14 and at least one pump module portion 16. In the embodiment depicted and described herein, two pump module portions 16 are provided. However, use of any number of pumping modules is contemplated depending on the requirements of the pump user. For example, FIG. 2 shows an infusion pump having four pumping modules 16.

Formed at the upper periphery of the main body portion 14 is a carrying handle 20. The main body 14 further includes a liquid crystal display (LCD) area 23 which conveys information about the pump to the user and provides for user interface with the pump, as described in more detail below. The main body 14 includes data-entry keys 25. The pump module 16 includes a tube-loading channel 27 and a display area 29 with a microprocessor. In a preferred embodiment, this microprocessor is a 68HC11 available from Motorola, Schaumburg, Ill. The main body portion 14 includes a slave microprocessor which is a slave to a master microprocessor. The slave microprocessor further includes an analog-to-digital converter (A/D converter). In a preferred embodiment, the master microprocessor is a 80C186EB available from Intel Corporation, Santa Clara, Calif. and the slave microprocessor is a 80C552 available from Philips Semiconductors, Sunnyvale, Calif. The slave microprocessor includes software in read-only memory (ROM) which drives the monitoring functions described below.

Figure 3:
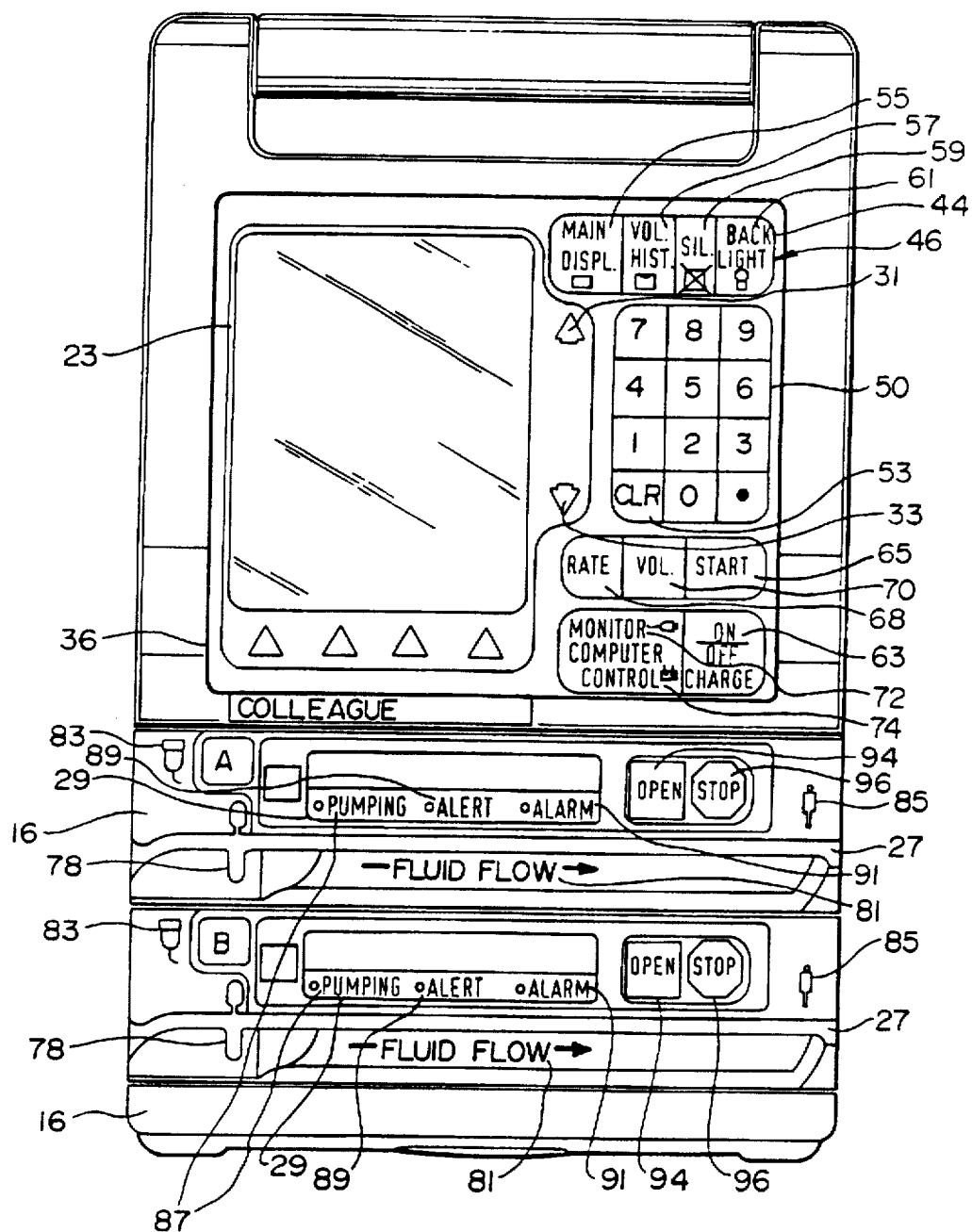
FIG. 3 is an elevational view of the infusion pump of FIG. 1, showing the detail of the pump face.

Referring to FIG. 3, an elevational view showing the detail of the face of the infusion pump 10 is seen. Contained along the side of the display area 23 are a scroll-up arrow key 31 and a scroll-down arrow key 33. These keys are used to select programming fields or actions within the display area 23. Contained beneath the display area 23 are a plurality of arrow keys 36 which are used to interact with selection alternatives in the display area 23. Because these arrow keys 36 are used in conjunction with the particular function displayed in the display area 23, these arrow keys 36 are referred to as "soft keys."

Figure 4:
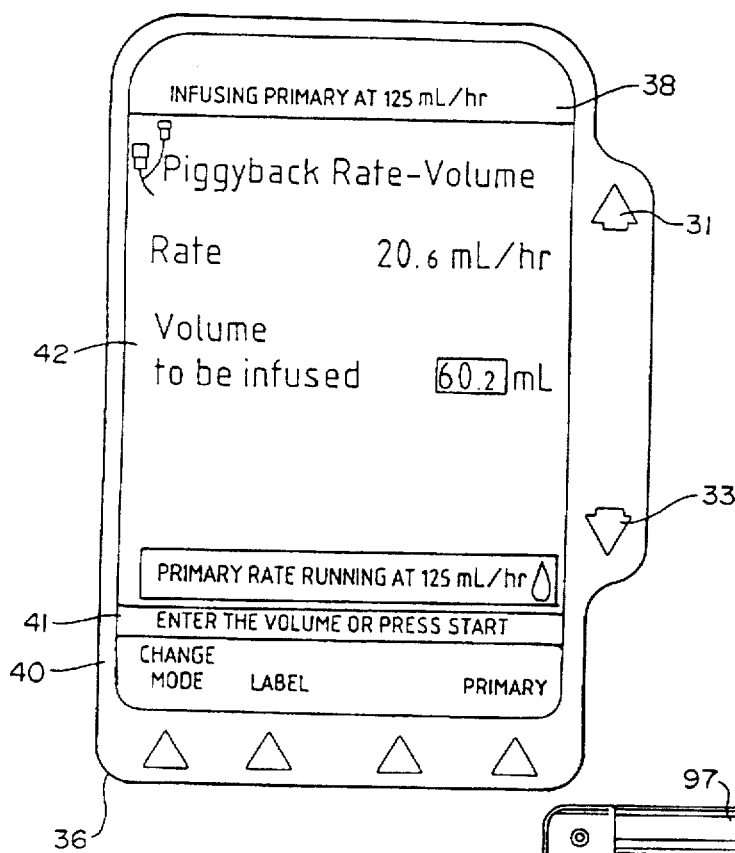
FIG. 4 is a detailed view of the display area of the infusion pump of FIGS. 1 and 2.

Referring now to FIG. 4, the display area 23 includes four display portions. Located at the top portion of the display area is the status display 38. The status display 38 gives the status of the pump infusion. The status display 38 also identifies alert, alarm, and failure conditions. Contained at the lower portion of the display area 23 is the prompt display. The prompt display includes a prompt line 41 which provides prompts or instructions for the user. A soft key area 40 is further provided which contains labels for the plurality of soft keys located beneath the display area 23. Thus, by following the prompts and making selections in accordance with the labels applied to the soft keys, the user can interface with the display screen. Finally, the middle portion 42 of the display area 23 is used for making infusion selections, programming, and displaying operating or running conditions of the pump infusion.

Referring back to FIG. 3, the main body 14 further includes a plurality of function keys 44. The function keys 44 include dedicated keys 46 which include user interface keys as well as a numeric key pad 50. Included in the numeric key pad 50 are the numbers zero through nine, and a decimal point key. These numeric and decimal point keys are used to enter programming values into the highlighted field in the display area 23, an example of which is seen in FIG. 4. The numeric key pad 50 further includes a clear key 53 which is used to clear values from the highlighted field. As a safety feature against inadvertent clearing of values from the highlighted field, if the clear key 53 is again pressed after the highlighted field has been cleared, the content of the field is restored to the last value stored in the master microprocessor.

The dedicated function keys 44 include a main-display function key 55. The main-display function key 55 is used to return the display area 23 to the initial or main display from any point in the user interaction. The volume-history function key 57 is used to display the volume history screen. The silence function key 59 silences pump alarms and pump alerts for a predetermined period, such as two minutes in the preferred embodiment. The back-light function key 61 serves one purpose when the pump 10 is plugged into an electrical outlet, and a related but second purpose when the pump 10 is on auxiliary battery power. When plugged into an electrical outlet, the back-light function key 61 turns the display back lights on and off. When on auxiliary battery power, the back-light function key 61 illuminates the display back lights, but in order to conserve power the back lights do not remain on after a predetermined period.

Included in the action keys is an on/off charge key 63. The on/off charge key 63 powers the infusion pump 10 on and off. When the pump 10 is infusing, pressing the on/off charge key 63 will provide a system override to stop the infusion. The action keys further include a start key 65. If all of the required programming values have been entered during the programming mode, the start key 65 initiates the infusion. Following an alarm notification, once the alarm condition is resolved the start key 65 cancels the alarm notification and restarts the infusion. The action keys further include a rate key 68, which is used to select the rate values, and a volume key 70, which is used to select the volume parameters when the infusion pump 10 is programmed for an infusion.

Two additional icons are used as indicators of pump conditions. The electronic-plug icon 72 indicates when the infusion pump 10 is plugged into an electrical outlet. The electronic-plug icon 72 also indicates that the auxiliary battery is being charged from the electrical power provided by the electrical outlet. A battery icon 74 is further provided, which is lit when the pump 10 is operating on auxiliary battery power, as described in detail below.

At least one pump module 16 is located beneath the main body 14 of the pump 10. The pump module 16 includes a tube loading channel 27 into which a standard IV tube 76 is loaded into the pump 10. The pump module 16 includes an automatic tube-loading feature. Contained within the tube-loading channel 27 is a keyed slot 78 adapted to receive a slide clamp 80 contained on the IV tube 76. The pump module 16 includes a free-flow prevention feature.

In order to assure that the IV tube 76 is loaded into the pump module 16 in the proper orientation, the pump module 16 contains several safety features. Initially, the slide clamp 80 is keyed such that it only fits into the keyed slot 78 in the proper orientation. Additionally, beneath the tube-loading channel 27, a fluid flow arrow 81 is provided to instruct the user as to the proper direction of fluid flow in the IV tube 76. Still further, on the left side of the pump module 16 an intravenous solution bag icon 83 is provided. This reminds the user that the end of the IV tube 76 that connects to the solution bag is to be directed to the left side of the tube-loading channel 27. Still further, on the right side of the pump module 16 is a patient icon 85. This icon 85 is used to remind the user that the end of the IV tube 76 that connects to the patient is to be directed to the right side of the tube-loading channel 27.

The pump module display area 29 further includes a character display area. In the embodiment depicted herein, an eight-character display area is provided. The display area is used to prompt or instruct the user during specific pump interaction operations. The display also is used during an alarm or alert condition to identify the particular condition. Finally, the display is used during infusion to provide an indication of the status of the infusion.

Contained beneath the character display area are three light-emitting diode (LED) status indicators. The first is a green LED 87 which indicates when the pump 10 is infusing. The second is a yellow LED 89 which indicates when the pump 10 is in an alert condition. The yellow LED 89 remains continuously lit during an alert condition, provided there are no active alarms. The third is a red LED 91 which indicates when the pump 10 is in an alarm condition. The red LED 91 flashes on and off during an alarm condition and remains lit continuously during a failure condition. If the infusion pump 10 is running on auxiliary battery power, the alert or alarm display will flash on and off in order to conserve battery power.

The pump module 16 also includes an open action key 94 and a stop-action key 96. The open action key 94 opens the loading mechanism so that an IV tube can be loaded into the tube-loading channel 27. When an IV tube is contained in the pump module 16, the open action key 94 opens the loading mechanism to allow removal of the IV tube. The stop-action key 96 provides a system override to stop any active infusion.

Figure 5:
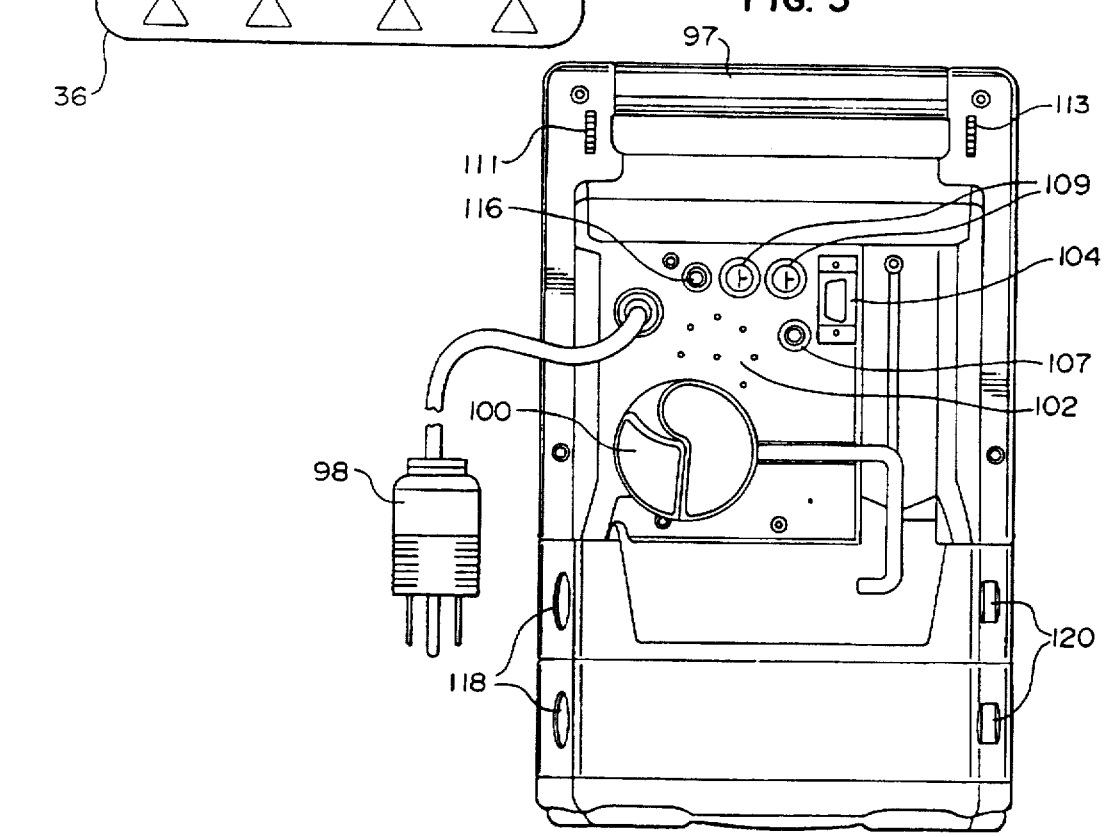
FIG. 5 is an elevational view of the rear of the infusion pump of FIG. 1.

Referring now to FIG. 5, the rear 97 of the infusion pump 10 is seen. The infusion pump 10 includes a grounded power cord 98 for plugging the pump 10 into a wall outlet to provide standard AC to power the infusion pump 10 and to recharge the auxiliary battery. The device further includes a mounting clamp 100 which is used to mount the pump 10 onto an IV pole 12. An audio speaker grill 102 is provided over an audio speaker which is used to generate alert and alarm condition audio tones. A communications port 104 is provided to allow the pump 10 to connect and communicate with a computer. The communications port 104 also can be used to communicate the nurse call signal to a computer located at a nurse station in a hospital. In the preferred embodiment, an RS 232 compatible interface is provided for external communications.

A DC receptacle 107 is further provided. The DC receptacle 107 enables the pump 10 to be connected to external DC power sources, such as for example, the 12-volt power source provided in most U.S. vehicles, to enable the pump 10 to be used with an ambulatory patient. The rear of the infusion pump 10 further includes fuse compartments 109 which contain electronic fuses as known in the art, an audio speaker volume control 111, and an LED contrast adjustment 113 for the main display. Further provided is a panel lock button 116. Enabling the panel lock button 116 disables the front panel keys to prevent inadvertent reprogramming as well as deliberate tampering with the pump 10.

Contained on the side of each pump module 16 is a manual-tube release knob 118. This knob 118 provides a manual override of the automatic tube-loading and unloading feature in the pump module 16. This allows the user to manually release the tubing from the pump 10. Further provided on each pump module 16 is a drop-sensor port 120. This port 120 allows for connection to the pump 10 of an optional drop sensor, which is used in conjunction with a standard drip chamber.

Referring now to FIGS. 6 to 10, the user interaction with the infusion pump 10 is described. As previously discussed, the user interaction is principally conducted through the pump display area 23, including the scroll up and scroll down arrow keys 31, 33 contained on the side and the soft keys 36 displayed underneath the display area 23.

Upon power-up of the pump 10 by pressing the on/off charge key 63, the pump self-diagnostic tests begin. The main display area 23 initially is lit, then goes dark, while the pump module display 29 illuminates each of the character positions. Next, the LEDs are lit and the audible speaker is activated, followed by the sounding of the back-up buzzer. This procedure enables the user to check for dark spots or lines on the display when the screen is lit, check for light spots or lines on the display when the screen is dark, ensure that the pump module display characters are appropriately lit, ensure that all of the LEDs are in working order, and hear that the audible speaker and back-up buzzer tone are active.

Figure 6A:
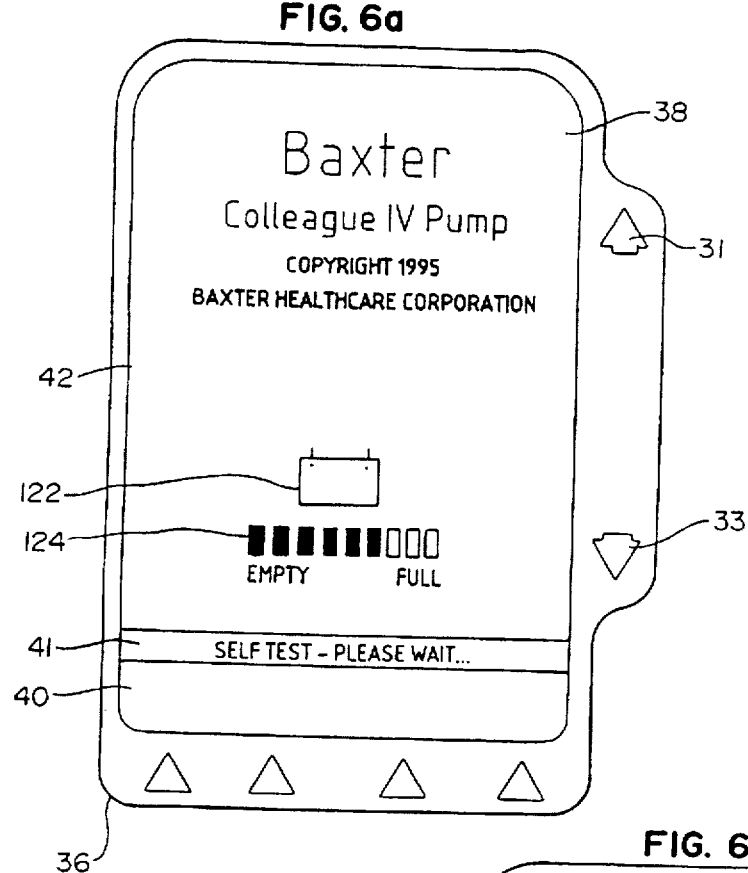
FIGS. 6a to 10b show the use interaction with the infusion pump of FIGS. 1 and 2.

Once the display area, LED, and speaker tests are complete, the screen displays the pump identification screen seen in FIG. 6(a). This screen includes a battery icon 122. The battery icon 122 includes a gauge 124 which graphically demonstrates the amount of amp hours remaining in the rechargeable auxiliary battery. In this initial screen, the prompt line 41 identifies that the pump self-diagnostic tests are proceeding and instructs the user to wait until the self-diagnostic tests are over.

Figure 6B:
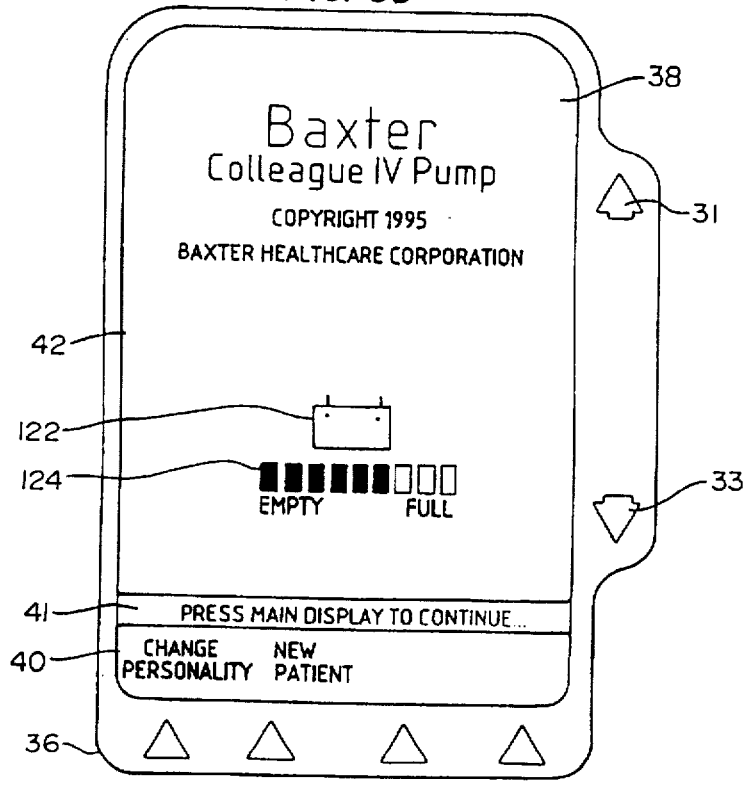
Figure 6C:
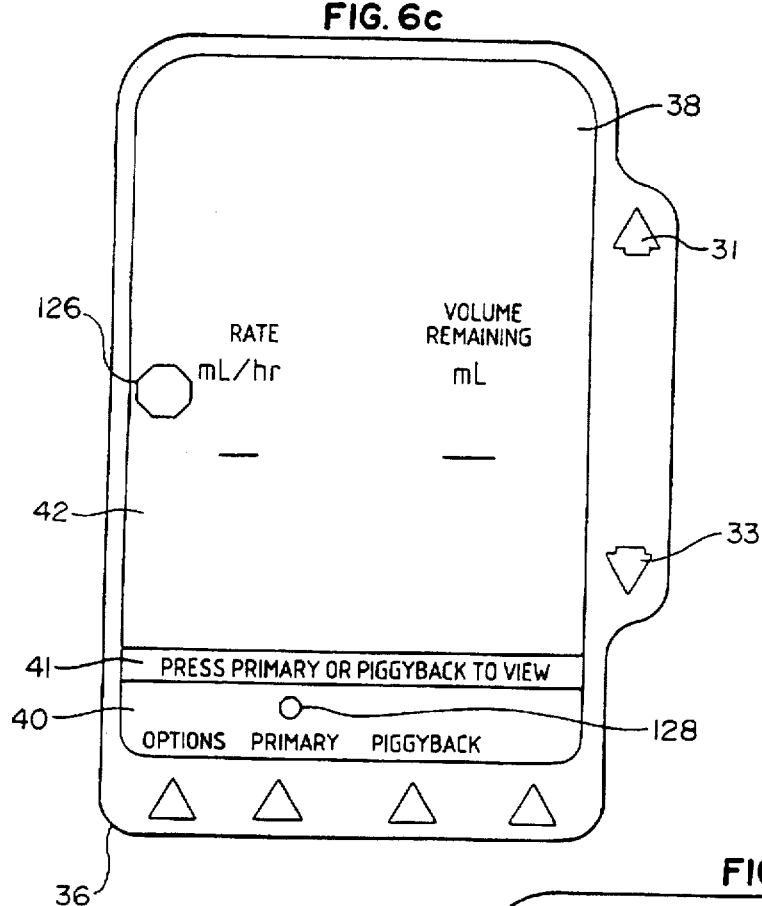

Referring now to FIG. 6(b), after the self-diagnostic tests are completed, the prompt line 41 instructs the user that the pump 10 is ready to continue into the programming mode. Additionally, several soft keys 36 are made available, depending on the configuration options chosen by the user. For example, in the embodiment depicted in FIG. 6(b), a soft key labeled "change Personality™" is present which enables the user to enter a programming mode to change the previously selected set of configuration parameters. Additionally, a soft key labeled "new patient" is present, indicating that information from a previous program is still retained in the memory. Pressing the "new patient" soft key will clear the programming memory and volume history from this previous patient. As instructed in the prompt line 41, pressing the main display key 55 advances the display area 23 to the main display screen.

Figure 7A:
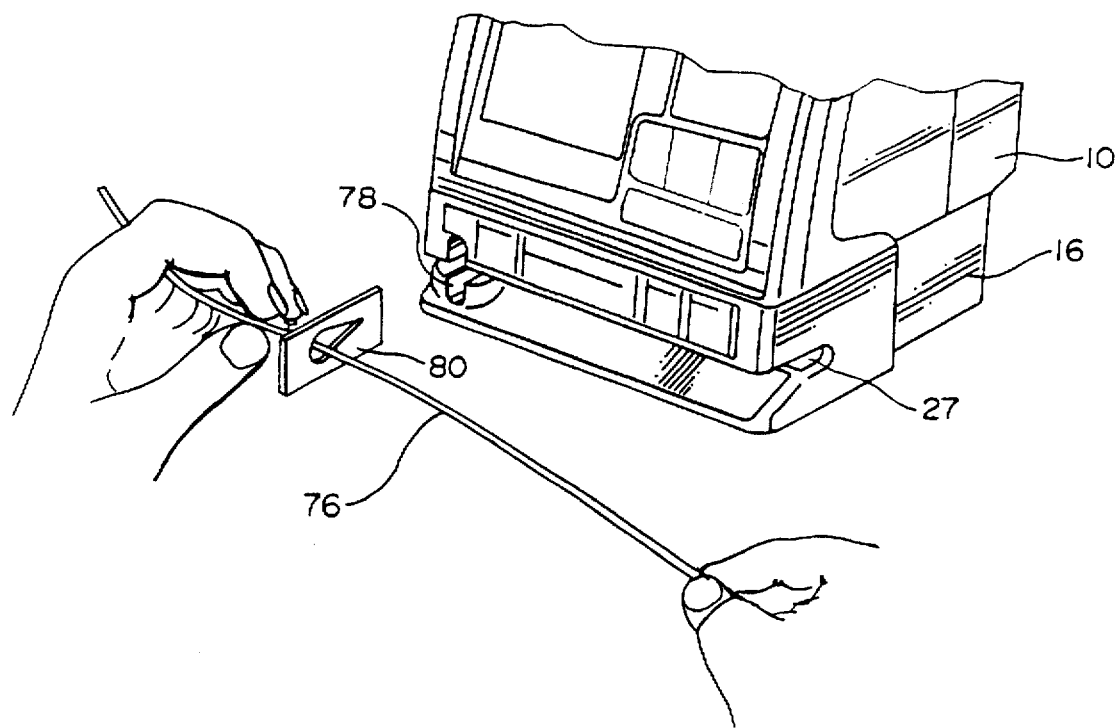
Figure 7B:
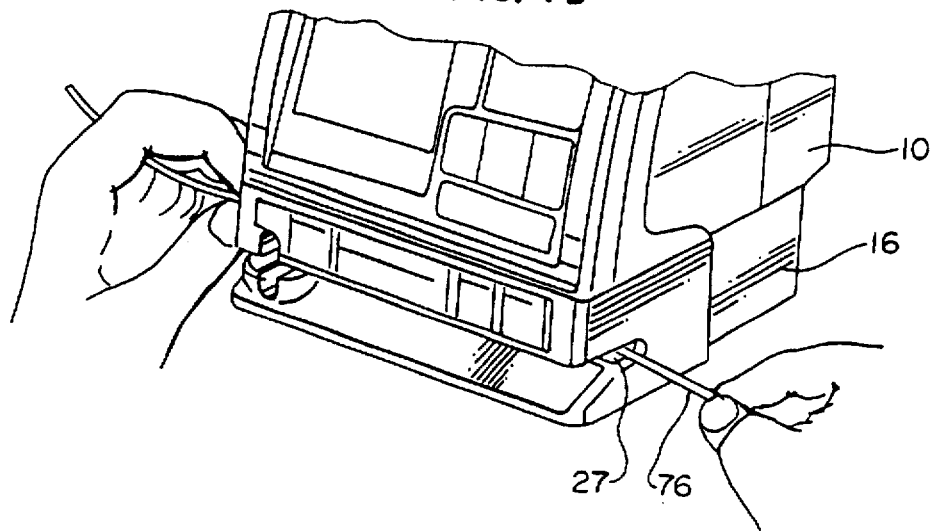

Prior to programming the infusion pump 10, the user is instructed to load an IV tube 76 into the pump module 16. Referring now to FIG. 7, the loading of the IV tube 76 into the automated tube-loading slot 27 in the pump module 16 is described. Initially, the open key 94 is pressed, which causes the automatic tube-loading mechanism to open. As seen in FIG. 7(a), the user positions the on/off slide clamp 80 into the keyed slot 78, which helps assure the proper orientation of the IV tube 76. Pulling the IV tube 76 taut, as seen in FIG. 7(b), the user slides the IV tube 76 into and along the tube-loading channel 27. Once the pump 10 detects the presence of the IV tube 76, the pump 10 automatically loads the IV tube 76 into the proper position in the pump drive mechanism. If the IV tube 76 is not loaded in a given predetermined time period after the open key 94 has been pressed, the automatic tube-loading mechanism will close to assure that an inadvertent loading of an improper IV tube does not occur. Additionally, when off, pressing the open key powers on the infusion pump 10 so that the IV tube 76 can be loaded into the device.

The main display screen includes the stop icon 126 which indicates that the pump 10 is not infusing. The soft keys 36 include an "option" key, a "primary" key, and a "piggyback" key. A stop icon 128 contained above the "primary" soft key indicates the default infusion. The display screen prompt instructs the user to press the "primary" soft key or "piggyback" soft key to view the programming mode for those two infusions.

Figure 6D:
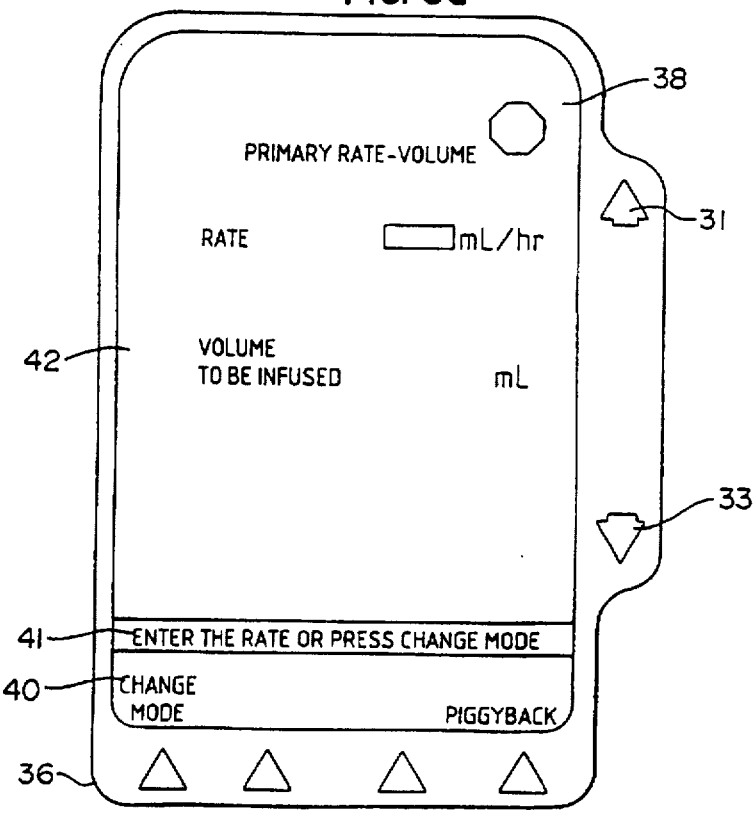

To begin programming the infusion pump, the rate key 68 is pressed, which changes the display to the rate-volume programming screen with the rate field highlighted, as seen in FIG. 6(d). If neither the "primary" soft key nor the "piggyback" soft key is pressed, the programming mode assumes the default infusion is to be programmed. The rate-volume programming screen prompt line 41 instructs the user to enter the rate or press change mode, while the soft key options include the "change mode" key and the "piggyback" key. Once the desired flow rate is entered by the user into the numeric key pad 50, either the volume or the arrow key can be used to highlight the volume field. The volume to be infused can then be entered by the user using the numeric key pad 50. For standard primary infusion, this completes the programming steps.

During programming, if incorrect values are entered by the user, pressing the clear key 53 clears the incorrect value so that the correct value can be programmed using the numeric key pad 50. To begin the infusion, the start key 65 is pressed. If the programmed values exceed an allowable range preprogrammed into the master microprocessor based on the particular set of configuration parameters chosen by the user, an out-of-range alarm will be activated upon pressing the start key 65.

When infusing, the display area 23 will show as a droplet icon an animated drop of water to indicate that the pump 10 is operational. The program rate of delivery, the volume of fluid remaining to be delivered, and/or the time remaining to deliver the remaining volume will be displayed. To stop an infusion before it is completed, the stop key 96 is pressed. The droplet icon will be replaced with the stop icon on the main display and the pump LED will no longer be illuminated. To restart the infusion, the start key 65 is pressed.

If the pump 10 is not restarted within a predetermined period of time, a channel stop alert will sound. The pump 10 also can be stopped if any alarm condition occurs or if the on/off charge key 63 is pressed while running. A piggyback infusion is stopped by closing the slide clamp 80 on the secondary infusion IV tube and pressing the stop key 96. To continue with the primary infusion, the "primary" soft key is pressed to change the operation mode of the pump 10, followed by the pressing of the start key 65 to begin the primary infusion.

Once the volume remaining to be infused reaches zero, indicating the infusion is concluded, the pump 10 will automatically enter a keep-vein-open (KVO) alert mode. During this alert mode, the pump 10 will continue infusing at the lesser of a preprogrammed KVO rate or at the programmed rate. To exit the KVO alert mode, the stop key 96 is pressed. The pump 10 can then be programmed for the next infusion, or the pump 10 can be powered off.

After the end of the infusion, to unload the IV tube 76, the open key 94 is pressed. The pump module 16 automatically closes the slide clamp 80 and opens the tube-loading channel 27 to allow removal of the IV tube 76. Upon removal of the IV tube 76, the auto load mechanism will close. Alternatively, if the IV tube 76 has not been removed after a predetermined time period, the mechanism will automatically close.

Figure 8A:
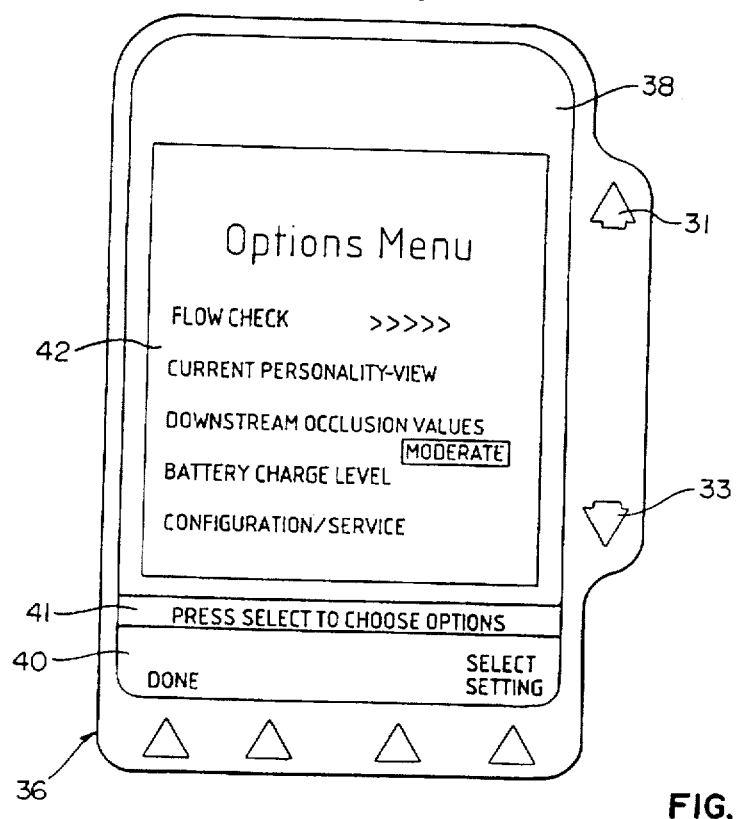

Referring now to FIG. 8(a), a pop-up window is seen which displays an options window if the "options" soft key is pressed from the main display. The options menu includes a flow check feature, a current Personality™ view feature, the selection of the downstream occlusion values, the battery charge level feature, and the configuration/service feature. In order to view the particular available features, the user highlights the feature to be viewed using the scroll-up and scroll-down arrow keys 31, 33. The current Personality™ view feature allows a quick review of the current set of configuration parameters.

Figure 8B:
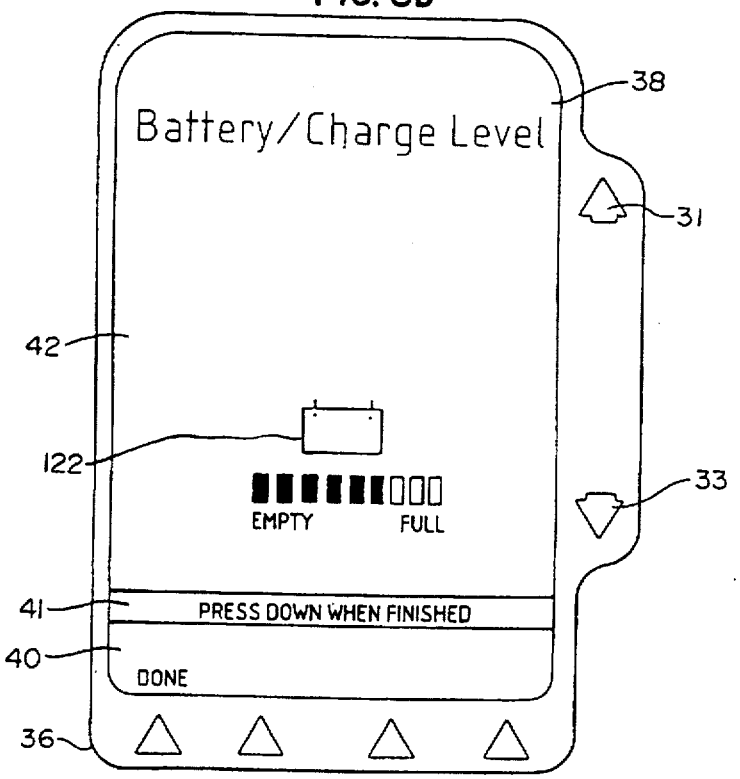

As seen in FIG. 8(b), the battery charge level on the options menu allows the user to access information regarding the battery charge level of the auxiliary battery. The battery charge icon 122 is displayed in the main display area. The prompt line 41 instructs the user how to exit the battery charge level option. A "done" soft key is provided to exit the battery charge level display.

The present invention also provides several troubleshooting alert, alarm and failure messages. When an alert, alarm or failure message occurs, the status area of the display, as well as the pump module character display, identifies the alert, alarm or failure. Alert messages may require a user intervention, but do not stop the infusion. Alarm conditions automatically stop the infusion and require immediate attention before infusion can be restarted. A device failure automatically stops any infusion. An alarm condition overrides an existing alert condition while a failure overrides all alerts and alarms.

An alert condition lights the yellow alert LED 89 beneath the pump module display, and sounds the alert tone. The alert tone can be silenced for a period of time, such as two minutes, by pressing the silence key 59. The alert conditions include a battery low alert, which indicates that the auxiliary battery has less than a predetermined amount of infusion time left, as described in detail below. This alert occurs before the battery alarm condition occurs. The battery depleted alarm indicates that the auxiliary battery charge has diminished below the level necessary to continue infusion, as described in detail below. To reset the battery depleted alarm, the infusion pump 10 must be plugged into an AC supply.

To configure the set of configuration parameters for the pump 10, the configuration/service function of the option menu seen in FIG. 8(a) is selected. Upon selection of the configuration/service function, a password entry screen seen in FIG. 9(a) appears. The password ensures that only proper hospital personnel access the configuration/service routine. The prompt line 41 directs entry of the password. The authorized personnel enters a numeral password in order to proceed in the configuration/service routine. The password entry screen includes a reference listing of the software version in the infusion pump 10. A "cancel" soft key is provided to exit the routine.

Figure 9A:
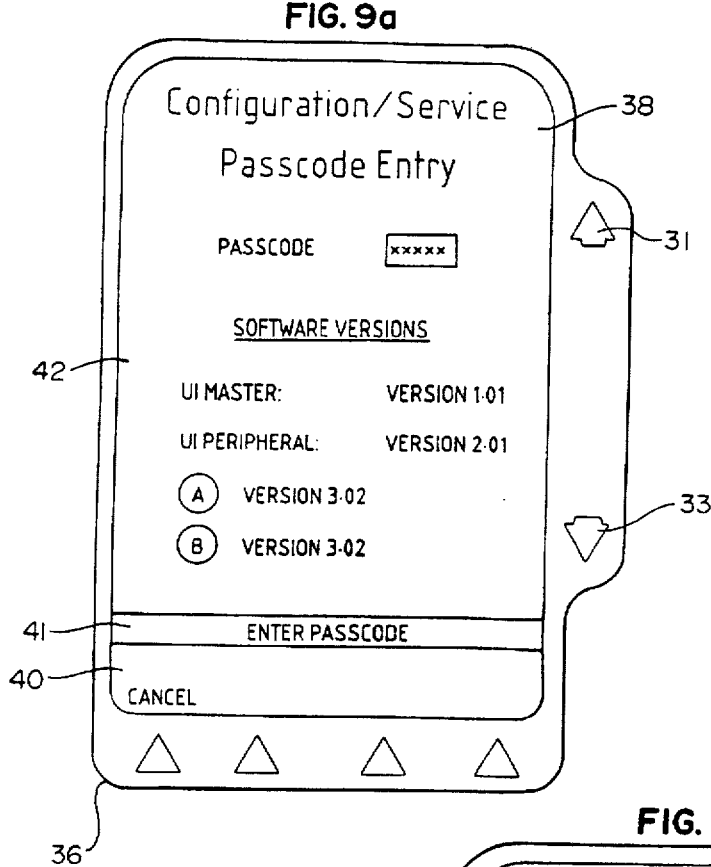
Figure 9B:
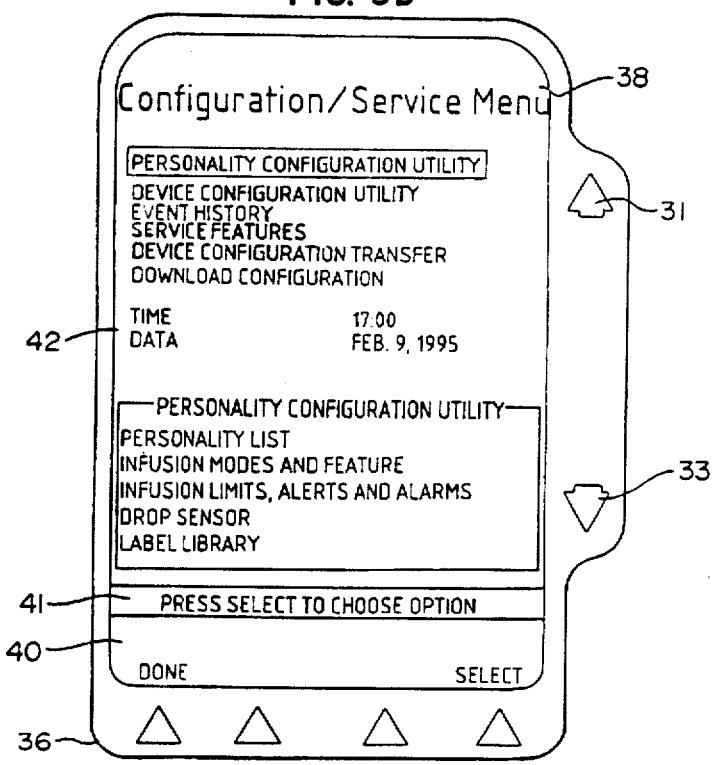
Figure 9C:
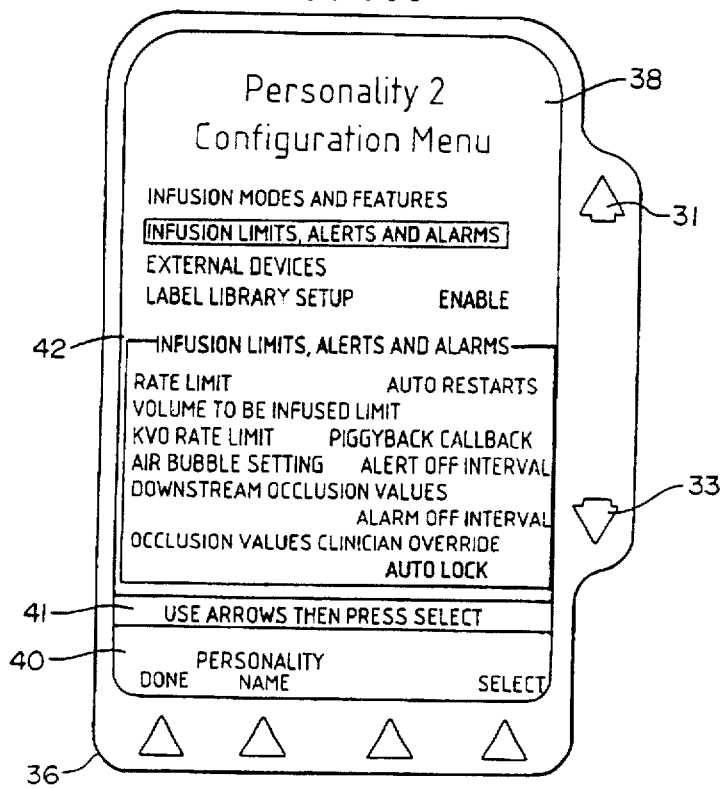

Upon successful entry of a valid password, a configuration/service menu screen as seen in FIG. 9(b) appears. The options include Personality™ configuration utility, device configuration utility, event history, service features, device configuration transfer, download configuration, time set and date set. When an option is highlighted, a message appears giving the particular components of an option. In the example seen in FIG. 9(b), the Personality™ configuration utility includes as components a Personality™ list, infusion modes and features, infusion limit alerts and alarms, drop sensors, and label library.

Figure 9D:
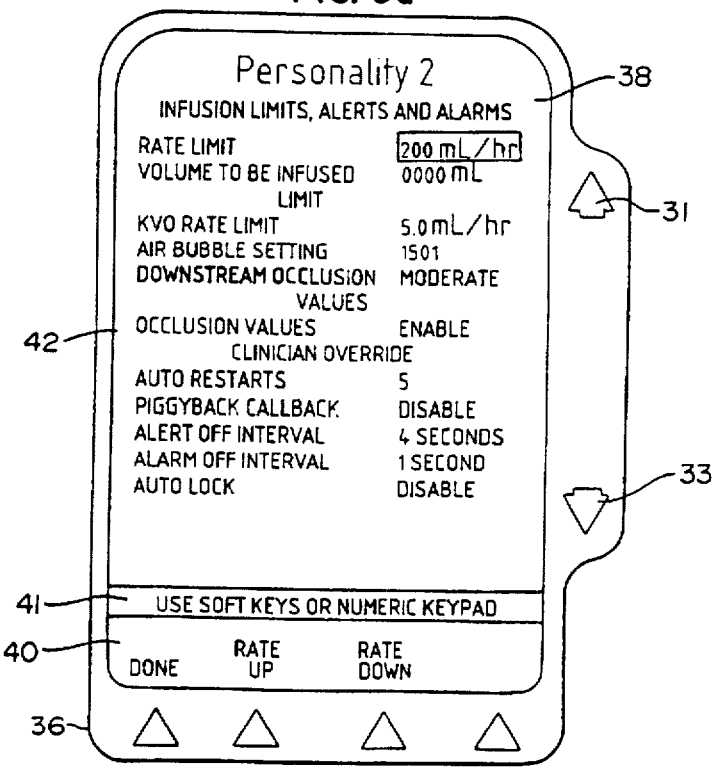

Authorized hospital personnel can program clinical feature limits and infusion alert and alarm characteristics. The infusion limits, alerts and alarms are accessed from the Personality™ configuration menu, seen in FIG. 9(c). Upon selection, the infusion limits, alerts and alarms menu seen in FIG. 9(d) is displayed. The settings in the Personality™ configuration menu apply to the infusion pump 10 as a whole and are not programmable for separate channels.

Figure 10A:
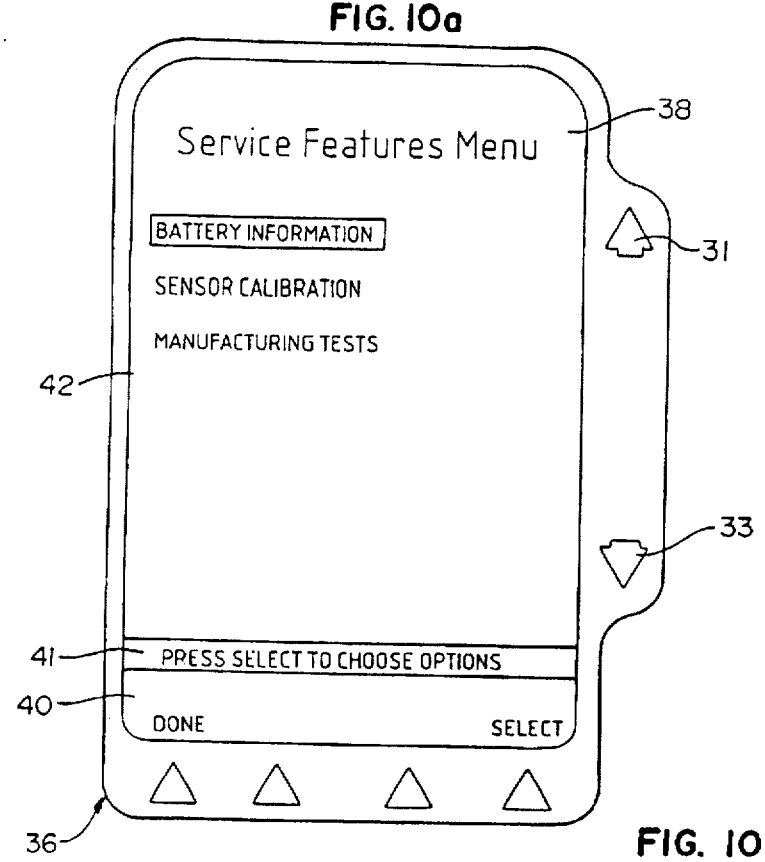
Figure 10B:
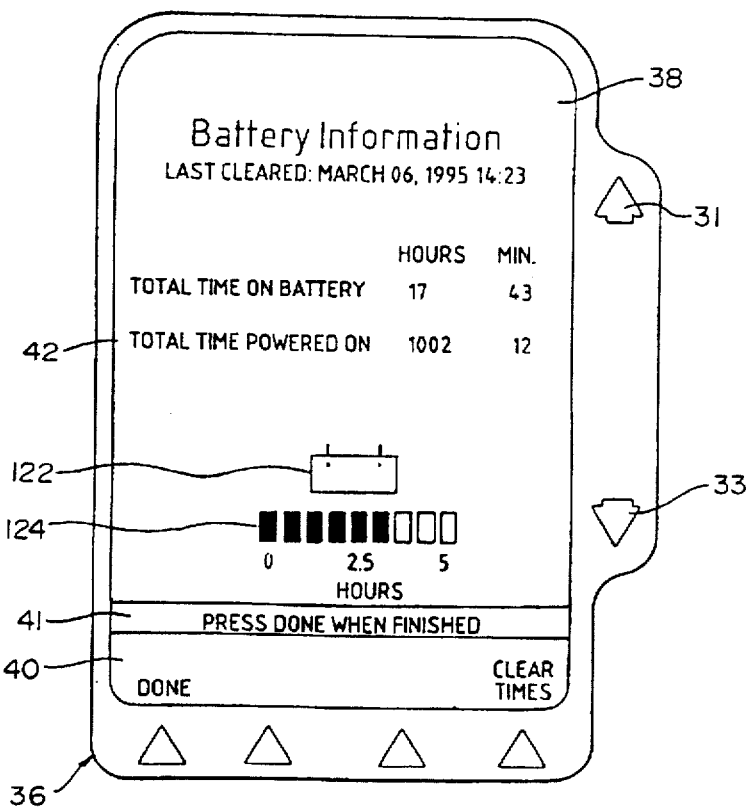

The infusion pump further includes service features which are accessible from the configuration/service menu. Upon selection of the service features, the service features menu seen in FIG. 10(a) is displayed. In the battery information selection, the slave microprocessor keeps track of a plurality of time periods related to battery operation. In the preferred embodiment, two parameters are tracked, including the total amount of time the infusion pump 10 is on and not plugged in, and the total amount of time the infusion pump is on. The battery information screen seen in FIG. 10(b) includes the battery charge icon 122, "done" and "new battery" soft keys, and the parameters. When a new battery is installed, the time parameters are cleared. The service features also include sensor calibration, which displays information related to the installation or replacement of certain infusion pump components, and manufacturing tests, which are used in the manufacturing process to calibrate infusion pump components.

Referring to FIG. 11, a block diagram of the battery gauge circuit is seen. A precise reference voltage 200 is provided. In a preferred embodiment, the reference voltage is 5 volts. The reference voltage 200 establishes the bias conditions required by the true RMS converter. The reference voltage 200 also provides the slave microprocessor A/D converter 202 with the reference voltage.

The precise reference voltage 200 is input into a buffer and level shifter 204. The buffer and level shifter 204 derives two reference voltages: a high-reference voltage 206 and a low-reference voltage 208. In a preferred embodiment, the high-reference voltage 206 is 5.7 volts and the low reference voltage 208 is 2.5 volts. The high-reference voltage 206 and the low-reference voltage 208 are input into a true RMS converter 210.

The battery gauge circuit further includes an analog electronic switch 212 which determines which of the four voltage/current ranges 214 is being measured. In a preferred embodiment, the switch 212 is an electronic multiplexer. The switch 212 is controlled by a control circuit 216 which also powers the gauge circuit on and off. The switch 212 sends to the true RMS converter 210 the selected signal. The true RMS output is conditioned by a conditioning circuit 218 prior to use as input into the A/D converter 202 of the slave microprocessor for analysis as described below.

Figure 12A:
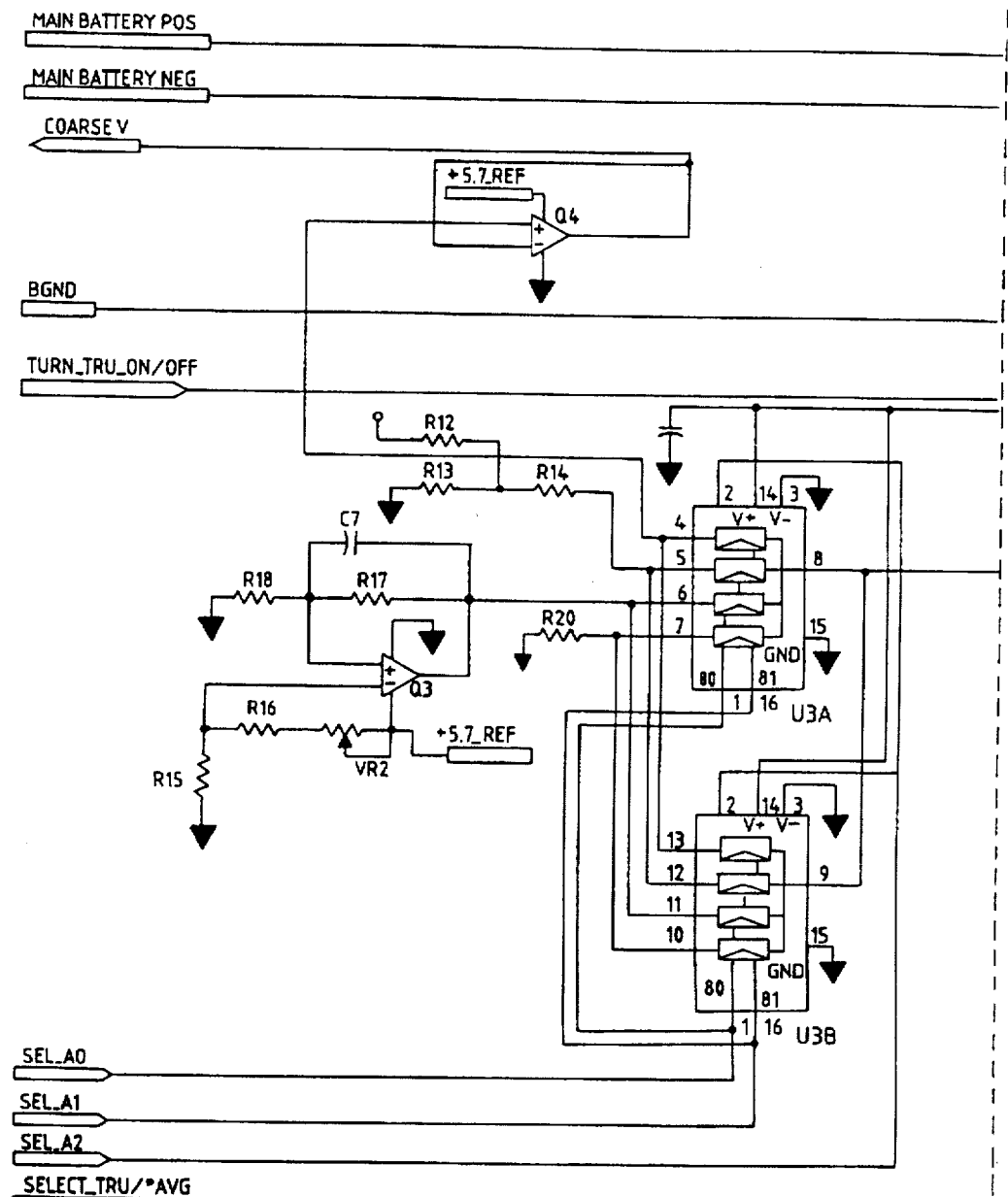
FIG. 12 (12a, 12b and 12c) is a schematic diagram of a battery gauge circuit constructed in accordance with the principles of the present invention.
Figure 12B:
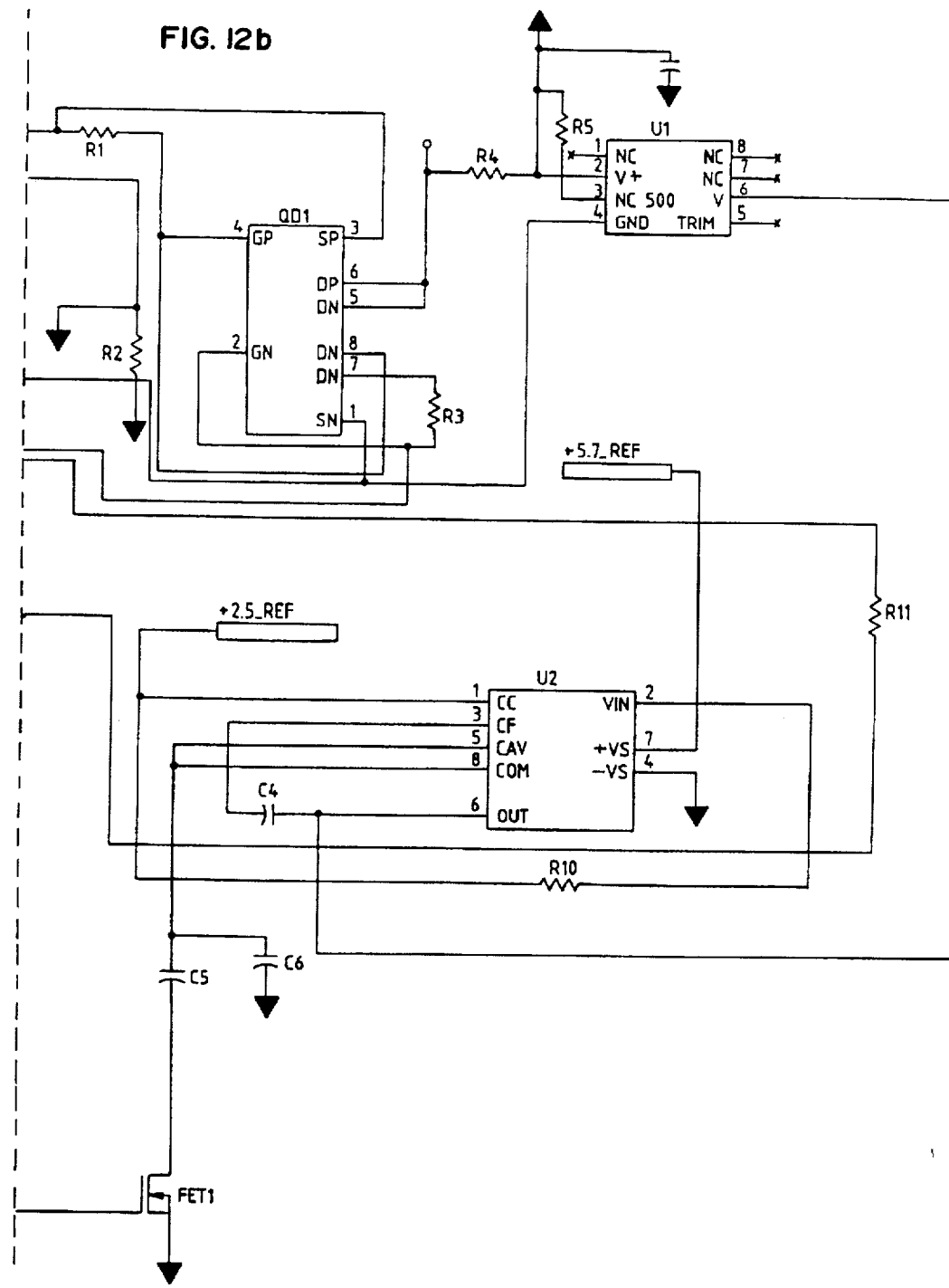
Figure 12C:
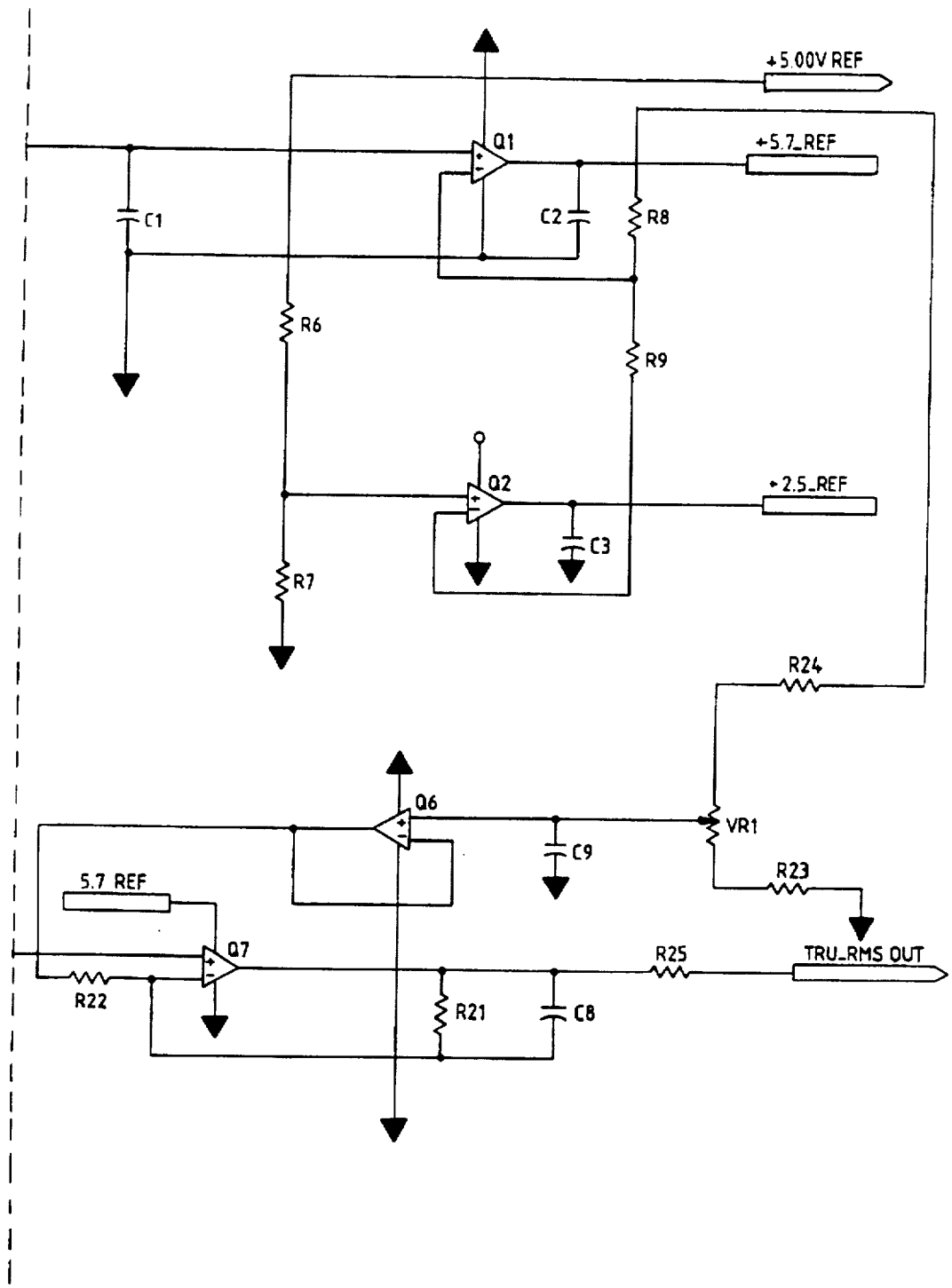

Referring now to FIG. 12, a schematic of a preferred embodiment of the battery gauge circuit is seen. The battery positive is input into a DC switch QD1 which, in a preferred embodiment, is an SI9942DY dual transistor available from Siliconix, Santa Clara, Calif. The S19942DY dual transistor has internal PFET and NFET transistors. In the preferred embodiment, the battery positive is input into the SP pin. The battery negative is set to ground via precision sensing resistor R2. When the unit is off, DC switch QD1 is normally pulled up by resistor R1 connected between the battery positive terminal and the gate input of DC switch QD1. To turn on the circuit, the GP input of DC switch QD1 must be pulled low. This is done by setting the DN output of DC switch QD1 low, which means gate input GN must be pulled high. Thus, if the control circuit signals a low input, the circuit is turned off. Correspondingly, if the control circuit signals a high input, the circuit is turned on. If the control circuit signal is open, resistor R3 performs a weak turn on to supply a 5-volt reference so that a slave microprocessor powers up properly.

The battery gauge circuit further includes a precision reference voltage regulator U1. In a preferred embodiment, the reference voltage is 5 volts and the reference voltage regulator U1 is an LT1021 DCS8-5 available from Linear Technology, Milpitas, Calif. In an alternative preferred embodiment, the reference voltage regulator U1 is an REF195GS available from Analog Devices, Norwood, Mass. The signal is applied to the V+ input of the voltage regulator U1 through resistor R4. Resistor R4 reduces power consumption and acts as short-circuit protection for the battery. A resistor R5 is provided if the reference voltage regulator includes a shut-down feature, such as in the REF195GS.

The precise reference voltage is input into the positive input of operational amplifier Q1 and is input via resistor R6 into the positive input of operational amplifier Q2. The precise reference voltage is further provided as a reference voltage to the slave microprocessor to be utilized as the A/D reference voltage. Operational amplifier Q1 provides as output a precise high reference which, in a preferred embodiment, is 5.7 volts. Operational amplifier Q2 provides as output a precise low reference which, in a preferred embodiment, is 2.5 volts. Support elements, including capacitor C1, resistors R6 and R7, capacitor C2, capacitor C3, and resistors R8 and R9, set and assure the precision and stability of the high and low references as known in the art. The supply voltage for operational amplifiers Q1, Q2, Q6 and Q7 is derived from the junction of resistors R4 and R5.

The battery gauge circuit further includes a true RMS converter U2. In a preferred embodiment, the true RMS converter U2 is an AD736JR available from Analog Devices, Norwood, Mass. The high reference is applied to the +VS input of the RMS converter U2. The low reference is applied to the CC input and the COM input of the RMS converter U2. Resistors R10 and R11 establish an offset bias to allow the RMS connector to perform the conversion from AC and DC input to true RMS DC output. Capacitor C4 is used for average mode filtering while additional capacitor C5 is used for additional true RMS filtering. The drain of field-effect-transistor FET1 is connected to capacitor C5 while the source is attached to ground. The gate of field-effect-transistor FET1 is connected to an input which is high for true RMS and low for average as applied by a slave microprocessor. When the signal at the gate of field-effect-transistor FET1 is high, the transistor conducts from drain to source to allow capacitor C5 to effect the true RMS filtering. Capacitor C6 is of a relatively small value and limits any high frequency interference noise present in the area from adversely affecting the performance of the circuit.

The battery gauge circuit further includes an analog switch U3, which selects the four inputs to the circuit. In a preferred embodiment, the analog switch U3 is an MAX309CSE available from Maxim Corp., Sunnyvale, Calif. The analog switch consists of two sections U3A and U3B. The four inputs are the high-voltage range, low-voltage range, high-current range and low-current range. The high-voltage range is derived from a voltage divider consisting of resistor R12 and resistor R13 off the battery, as derived from the output of DC switch QD1, which is input into the 4 and 13 pins of analog switch U3. The low-voltage range is derived from the voltage divider made up of resistors R12, R13, through adjusting resistor R14, input into the 5 and 12 pins of analog switch U3. In practice, the four selections are unique and no leakage or cross talk occurs between the four selections.

The low current indication is supplied from operational amplifier Q3, the output of which is input into the 6 and 11 pins of analog switch U3. Resistor R15 and resistor R16 set the offset of operational amplifier Q3, while resistor R17 and resistor R18 set the gain of operational amplifier Q3. Resistor R16 also may include a second rheostat VR2 for setting the output to mid range. Capacitor C7 limits any high frequency interfering noise present in the area from adversely affecting the circuit. The source voltage for this driver is obtained from the difference in voltage across resistor R2. The high current range is set by resistor R20 and is input into the 7 and 10 pins of analog switch U3 and also derives its source voltage from the difference in voltage across resistor R2.

A coarse voltage signal also is supplied to the slave microprocessor so that measurements of battery voltage can be made when the high-voltage or low-voltage measurements are not being made and acts as a second check on the battery gauge. The coarse voltage signal is output from operational amplifier Q4 the positive input of which is derived from a voltage divider made up of resistors R12, R13. This voltage is used by the slave microprocessor for detecting pump alarms due to voltage decreases. The voltage supplied to resistor R12 is derived from pins 5 and 6 of switch QD1.

The true RMS output from the RMS converter U2 is conditioned by operational amplifier Q6 and operational amplifier Q7 prior to input into the A/D converter. Operational amplifier Q6 acts as a zero-impedance feed into the resistor gain network made up of resistor R21 and resistor R22. When the high-current range is selected and the battery is disconnected, a rheostat VR1 is adjusted for the midrange voltage. Resistor R23 and resistor R24 refine the range of adjustment of rheostat VR1. Capacitor C8 limits noise present in the area from adversely affecting the circuit. Capacitor C9 stabilizes operational amplifier Q6. The conditioned true RMS signal is supplied to the A/D converter through resistor R25. After rheostat VR1 is adjusted, rheostat VR2 is adjusted for the mid-range voltage when the low current range is selected.

The battery gauge circuit provides input to the slave microprocessor so that the battery-monitoring process portion of the battery gauge can occur. The battery-monitoring process has four critical states: Battery Alert; Battery Alarm; Battery Depleted; and Battery Overcharge. A Battery Alert is generated when less than a predetermined time is left until the Alarm is generated. In a preferred embodiment, this predetermined time is 30 minutes. A Battery Alarm occurs when the battery voltage falls below a critically determined value. In a preferred embodiment, this critical value is 10.8 volts. The Battery Deplete alarm is generated when the battery falls below a battery-depleted value. In a preferred embodiment, the battery-depleted value is either 10.4 volts or 0.25 amp hours remaining. The Battery Overcharge occurs when the battery has overcharged, as described in detail below. In the preferred embodiment, the auxiliary battery is an NP2-12 available from Yuasa Battery America, Santa Fe Springs, Calif.

Figure 13:
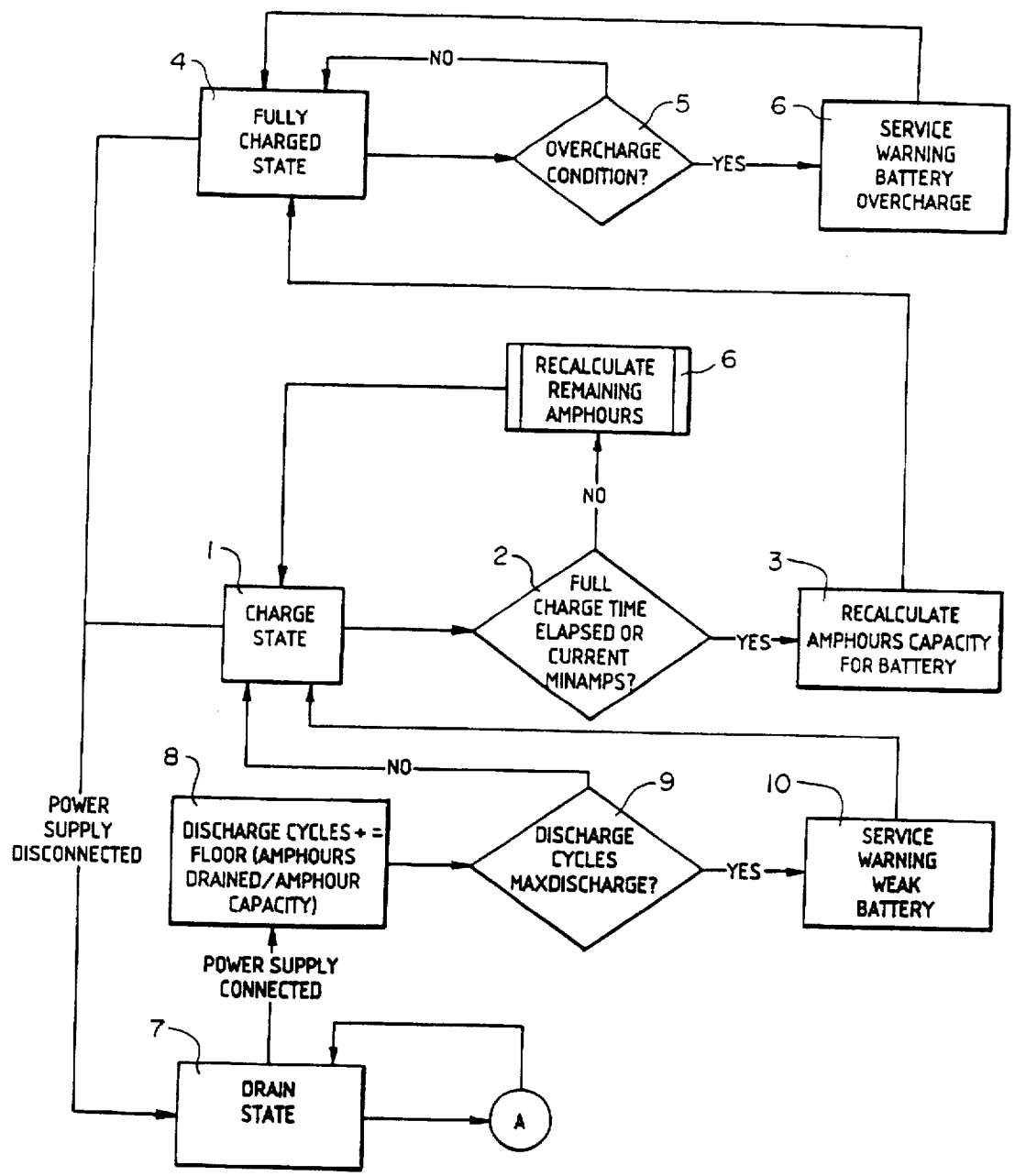
FIG. 13 is a flow chart of a battery-monitoring process constructed in accordance with the principles of the present invention.

Turning now to FIG. 13, a flow chart depicts the states in which the battery-monitoring process of the battery gauge may be found and the steps through which the battery gauge progresses. In step 1 (the Charge State), the battery gauge is monitoring the auxiliary battery, which is charging because it is connected to a wall outlet. Periodically throughout this step, the battery gauge will sample inputs read from the auxiliary battery. In step 2, the gauge, having read these inputs, compares the total time elapsed since the battery began charging with the time required to fully charge the battery. In a preferred embodiment, the time required to charge the battery from a full depletion is fifteen hours. This figure would be adjusted for batteries of different capacities or for batteries which have not completed a full discharge cycle prior to entering the charging state. Step 2 also determines if the current drawn by the battery is less than a minimum amperage. In a preferred embodiment, this minimum amperage is 4 ma. If either the time charging or the current drawn indicates the battery has been fully charged, the maximum amp hour capacity for the battery will be calculated in step 3.

Figure 15:
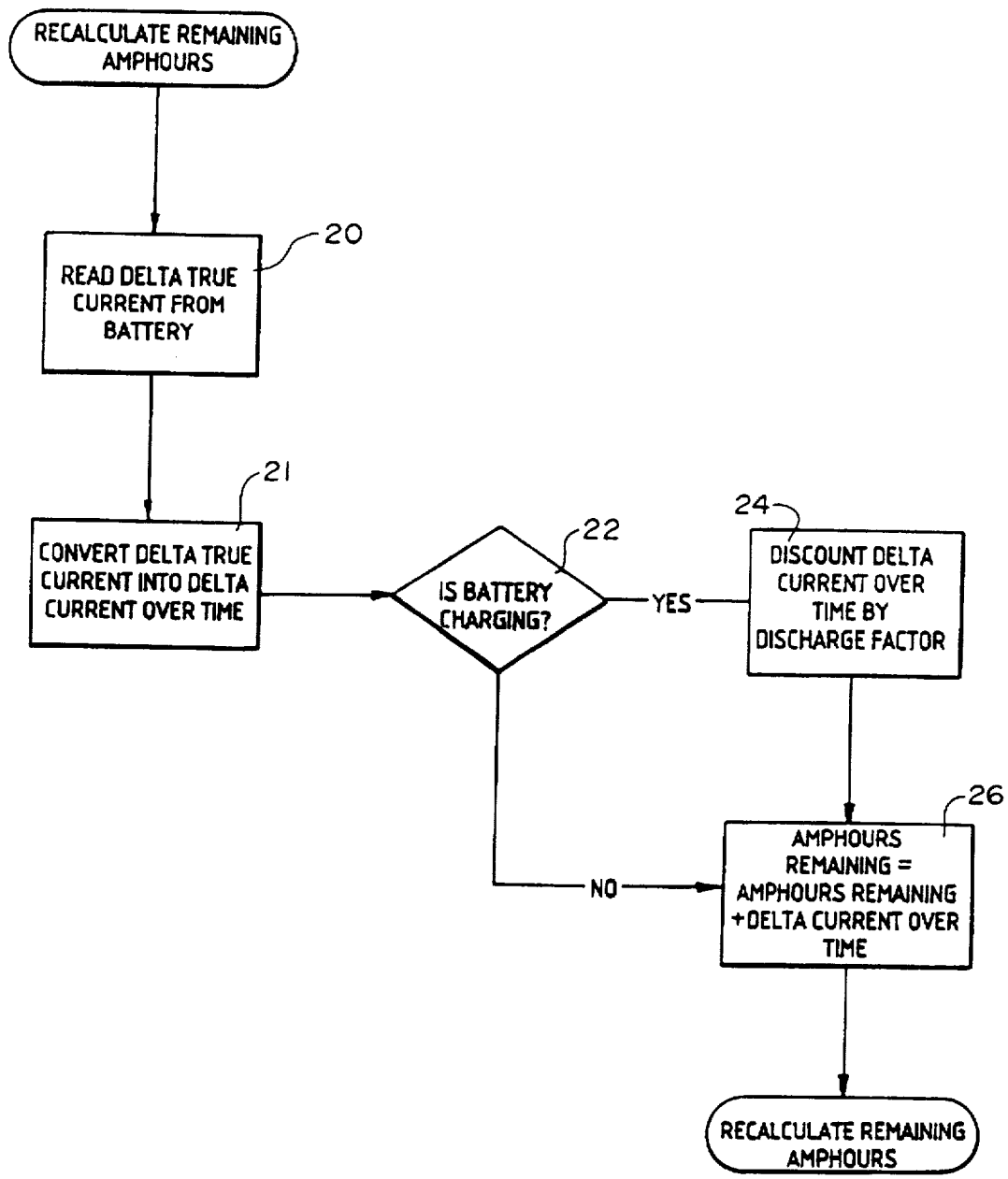
FIG. 15 is a flow chart a of remaining time process constructed in accordance with the principles of the present invention.

The battery capacity is recalculated by interpolating between a minimum and a maximum amp hour capacity for the battery based on the number of discharge cycles. In a preferred embodiment, the maximum capacity is 1.9 amp hours (for a new battery) and the minimum is 1.3 amp hours. The interpolation is done on a linear basis with a maximum of 150 discharge cycles representing 1.3 amp hours. The interpolated value is then averaged with the actual number of amp hours that have been calculated throughout the charging cycle based on current into the battery, as shown in FIG. 15 and described below. When the battery capacity has been recalculated, the battery gauge will enter step 4 (the Fully Charged State). If the battery has not been fully charged, the remaining amp hours in the battery will be calculated in step 6, as shown in FIG. 15 and discussed below. When the remaining amp hours have been calculated, the battery gauge will return to step 1.

From step 4, the battery gauge will periodically monitor to detect an overcharge condition. In a preferred embodiment, an overcharge condition exists if the current decreases below 50 ma and then rises above 50 ma or if the charging voltage of the battery exceeds 14.1 volts. If an overcharge condition is detected in step 5, the battery gauge will set a service alert in step 6, the alert will be displayed or deferred until the next power on of the infusion pump.

The inputs are received from the A/D converter of the slave microprocessor as count readings. In a preferred embodiment, the inputs include low current, high current, low voltage, high voltage and coarse voltage. The count read for the various inputs is converted by the microprocessor into a voltage or milliamperage reading which may be displayed or used for further calculations. The maximum count value is a distinguished input which reflects any error in monitoring the battery and which is not converted.

While in accordance with the principles of the present invention there need only be one current input and one voltage input, in the preferred embodiment, the high current is initially sampled. If this value is in a predetermined low-current value, the value is discarded and the low current is subsequently used in its place. Likewise, in the preferred embodiment the low-voltage is sampled. If the coarse voltage is less than a predetermined low voltage range, the low battery gauge voltage is selected; otherwise the high voltage is sampled. In the preferred embodiment's steady state, the use of either high or low inputs may be changed as the sampled values cross the thresholds. In a preferred embodiment, the low-current value is in the ±370 ma range and the low voltage is less than 13.05 volts.

From either step 1 or step 4 the battery gauge will be transferred to step 7 (the Drain State) upon disconnection from the wall outlet while the infusion pump remains in power-on mode. If in the power-off mode when the infusion pump is disconnected from the wall outlet, the number of remaining amp hours, the number of discharge cycles and the date are stored for later use, but no new actions are taken until the infusion pump is powered on. When the infusion pump is powered on again, the amp hours remaining will be discounted by a percentage for the time the battery has been powered off. In a preferred embodiment, the discount is 2% per month.

The battery gauge leaves step 7 when the infusion pump is reconnected to a wall outlet. Upon pump reconnection to a wall outlet, the battery gauge recomputes the number of discharge cycles the battery has passed through. This is done in step 8 by adding the number of quarter-discharge cycles (rounded down to the next lowest quarter-discharge) to the previously stored number of discharge cycles. The new total number of discharges is compared in step 9 to a maximum number of discharges. In a preferred embodiment, this number of discharges is 150. If the new number of discharges exceeds this number, a service alert is issued in step 10. Whether or not such an alert is issued, the battery gauge then enters step 1 (the Charge State), the effect of which is described above.

Figure 14:
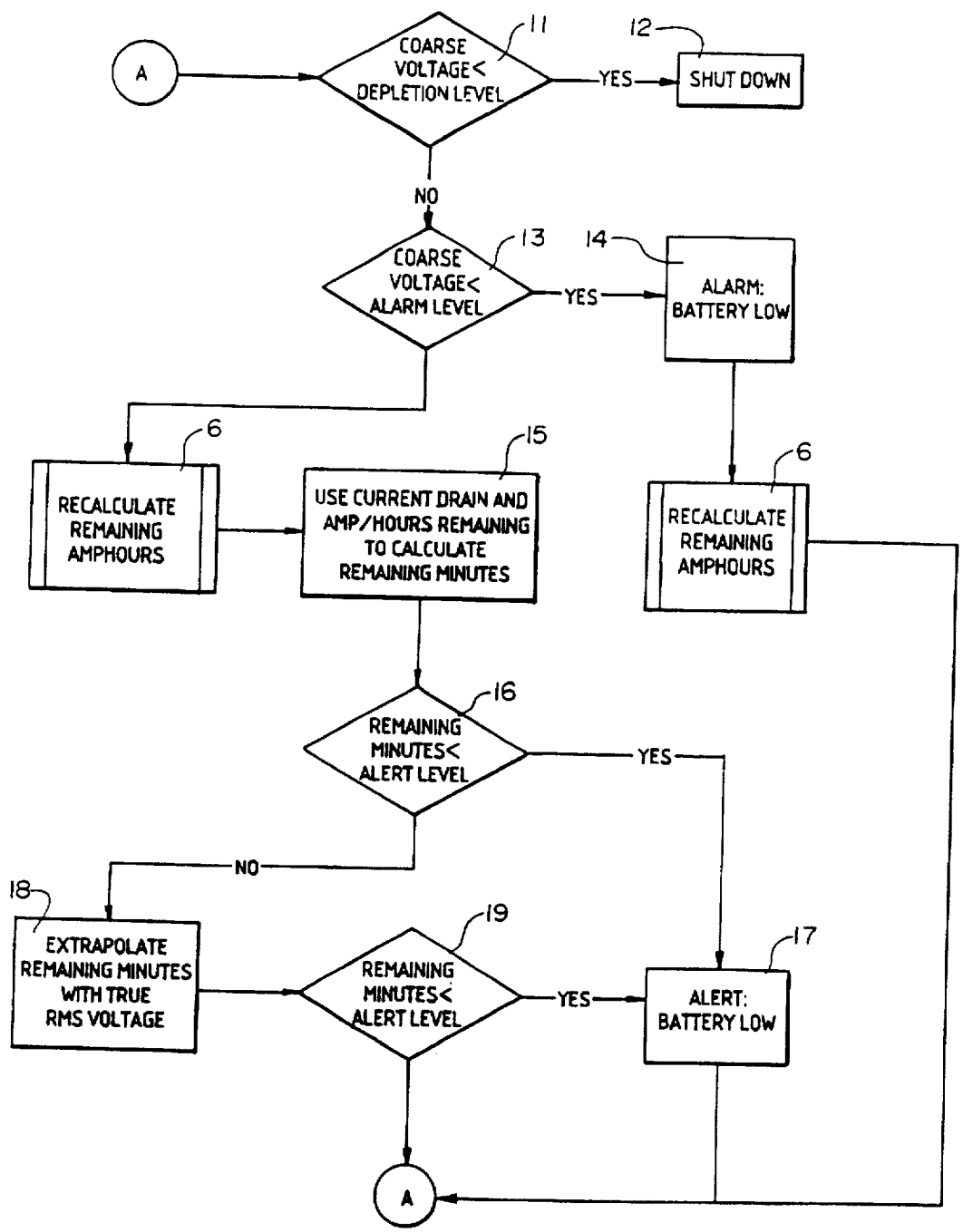
FIG. 14 is a flow chart of a battery life process constructed in accordance with the principles of the present invention.

While in step 7, the battery gauge periodically monitors the remaining life of the battery. The steps it takes are shown in FIG. 14. The first step 11 samples the coarse voltage and compares it with an absolute minimum below which damage will be done to the battery. In a preferred embodiment, this voltage is 10.4 volts. If the coarse voltage is below this threshold, the device is shut down in step 12. If the coarse voltage is above the absolute minimum threshold, the coarse voltage is compared with a higher voltage threshold in step 13. In a preferred embodiment, the threshold is 10.8 volts. If the coarse voltage is below this higher threshold, an alarm is activated in step 14. This alarm is reset only upon reconnection of the infusion pump to the wall outlet. If the alarm is reset, the battery gauge then recalculates the remaining amp hours in the battery, as shown in FIG. 15 described below. The battery gauge then returns to the Drain State, shown in FIG. 13, step 7.

If the coarse voltage thresholds in steps 11 and 13 are not crossed, the battery gauge then recalculates the remaining amp hours in the battery, as shown in FIG. 15 described below. With this information, in step 15, the battery gauge calculates the remaining minutes left in the battery.

In step 16 the remaining time is compared to a minimum threshold time remaining. In a preferred embodiment, this minimum time remaining is thirty minutes. If the remaining time as calculated in steps 15 and 16 is less than the minimum threshold time remaining, in step 17, the battery gauge registers an alert that the battery is low. This alert is reset only upon reconnection of the infusion pump to the wall outlet.

If the remaining time as calculated in steps 15 and 16 is greater than or equal to the minimum threshold time, the time remaining is recalculated in step 18 using true RMS voltages sampled over time. This compensates for the effect of spaced, unequal impulses going into the infusion pump, which can cause a single voltage reading to not accurately to reflect the battery usage. Thus, the invention extrapolates the time remaining based on a series of true RMS voltage samples over a period of time.

In a preferred embodiment, the voltage samples are accumulated to cover a period of six minutes. Six voltage values are stored, each of which represents the average of 10 true RMS voltage samples taken at six-second intervals. In a preferred embodiment, the extrapolation is done linearly, although in an alternative preferred embodiment a higher-level extrapolation can be made, either exactly or by adjusting the linearly computed time remaining according to a known factor reflecting the non-linearity of the impulse behavior.

In the preferred embodiment, the slope and intercept are calculated according to the following formulas:

$$B=((\Sigma XY)-(n*\bar{Y}))/((\Sigma X^2)-(n*\bar{X}))$$

and $$A=\bar{Y}-(B*\bar{X})$$

where:

A is the intercept of voltage at time 0, i.e., six minutes before present;

B is the slope of the voltages over time;

$\Sigma XY$ is the summation of each voltage reading (Y) multiplied by its time position (X) (time positions are measured from 1 to 6, with time 6 being the most recent);

n is the summation of all time position values (i.e., 1+2+3+4+5+6=21);

$\Sigma X^2$ is the summation of the squares of all time position values (i.e., 1+4+9+16+25+36=91);

$\bar{X}$ is the average of all time position values, or six in the preferred embodiment; and $\bar{Y}$ is the average of all voltage values, or six in the preferred embodiment.

In the preferred embodiment, six voltage values spaced at six minutes are used so that the above equations can be simplified by the replacement of certain values by the constants derived above. Thus, in the preferred embodiment, the formulas reduce to:

$$B=((\Sigma XY)-(21*\bar{Y}))/17.5$$

and $$A=\bar{Y}-(B*3.5)$$

Further simplification of the calculations required is done by keeping the voltage values in a ring buffer in order to facilitate the addition of a new value and the removal of an old value at every minute interval. Finally, the time left to any voltage (V) can be calculated according to the following formula:

$$T=((V-A)/B)-6.$$

where:

T is the time left to reach any voltage used in the formula, in minutes. In the preferred embodiment, the voltage used in this formula is 10.4 volts.

Once the remaining minutes have been calculated as described above, the battery gauge again compares the time with a minimum threshold time remaining. In a preferred embodiment, this minimum threshold time remaining is 30 minutes. If the remaining time as calculated in step 19 is less than the minimum threshold time remaining, then in step 17, the battery gauge registers an alert that the battery is low. This alert is reset only upon reconnection of the infusion pump to a wall outlet. In a preferred embodiment, this extrapolation can necessarily only take place once the battery has been in a drain state for six minutes. Prior to that time, the battery gauge will issue an alert if less than 11.8 volts remain in the battery, as determined by the coarse voltage sample.

Regardless of whether the battery gauge registers an alert in step 17 or the comparison in step 19 determines that there is enough time left in the battery, the battery gauge returns to the Drain State, as shown in FIG. 13, step 7.

Turning now to FIG. 15, the means for recalculating the remaining amp hours in the battery is shown. In step 20, the battery gauge samples the true current through the battery and subtracts the previously sampled true current and stores the result as delta true current. Depending on the time between samples, which in a preferred embodiment is six seconds, the battery gauge will calculate the change in current over a standard unit of time in step 21. In step 22, the battery gauge determines if the battery is in charging state. In a preferred embodiment, the battery will always draw a small amount of current, less than or equal to 4 ma, even if fully charged. Therefore, the battery will be considered to be charging when the battery is drawing more than 4 ma. If the current readings and therefore current over time readings are negative, the battery is draining. The battery should not be draining if the battery is connected to the wall outlet. In a preferred embodiment, a signal is set when the power supply is connected. If a battery drain is occurring in this state, then a failure is issued.

In step 24, which is reached only if the battery is charging, the change in current over time is discounted by a battery-dependent factor based on the number of partial discharges that the battery has experienced. In a preferred embodiment, the discount is a percentage from 0–15% that is linearly interpolated based on the number of discharge cycles that the battery has gone through. In step 26, the battery gauge adds the change over time to the stored amp hour value, completing the process.

It should be understood that various changes and modifications to the preferred embodiment described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An infusion pump comprising:
 a pump drive mechanism for applying the pumping action to a liquid for infusion in a patent;
 a battery for powering the pump drive mechanism;
 a circuit which monitors the voltage and current from the battery;
 a circuit responsive to the monitoring circuit which determines the remaining time of charge in the battery;
 a battery alarm which occurs when the remaining time of charge in the battery is below a predetermined level;
 a battery low alert which occurs when the remaining time of charge in the battery is below a predetermined level but above the battery alarm level; and
 display means for displaying the remaining time of charge in the battery.

2. The infusion pump of claim 1 wherein the monitoring circuit means further includes means for sampling the voltage and the current of the battery.

3. The infusion pump of claim 1 wherein the monitoring means further includes means for alternatively sampling the voltage of the battery and the current from the battery.

4. The infusion pump of claim 1 further including a battery low alert which occurs when the battery charge is below a predetermined level.

5. The infusion pump of claim 1 further including microprocessing means responsive to the determining circuit which calculates the remaining minutes of charge left in the battery.

6. An infusion pump comprising:
 an electrically powered pumping mechanism which provides pumping action for infusing a patient with a liquid;
 a battery which provides electronic power to the electronically powered pump mechanism;
 a circuit which monitors the voltage of the battery;
 a circuit which monitors the current from the battery;
 means responsive to the current-monitoring circuit and the voltage-monitoring circuit which determines the remaining time of charge in the battery;
 a battery alarm which occurs when the remaining voltage left in the battery is below a predetermined level;
 a battery low alert which occurs when the remaining time of charge in the battery is below a predetermined level;
 a battery deplete alarm which occurs when the battery voltage or current falls below a predetermined battery deplete level; and
 a display which displays the remaining time of charge in the battery.

7. The infusion pump of claim 6 wherein the current-monitoring circuit and the voltage-monitoring current utilize the same circuit.

8. The infusion pump of claim 6 further including microprocessing means responsive to the determining circuit which calculates the remaining minutes of charge left in the battery.

9. A method of infusing a liquid into a patient comprising:
 infusing the liquid into the patient by use of an electrically powered mechanism;
 powering the electronically powered mechanism with a battery;
 monitoring the voltage of the battery;
 monitoring the current from the battery;
 determining from the voltage and the current the remaining time of charge in the battery;
 alarming when the remaining time of charge in battery is below a predetermined level;
 alerting when the remaining time of charge in battery is below a predetermined level but above the battery alarm level; and
 displaying the remaining time of charge in the battery.

10. The method of claim 9 wherein the step of monitoring the voltage of the battery further includes sampling the voltage of the battery.

11. The method of claim 10 wherein the step of monitoring the current of the battery further includes sampling the current of the battery.

12. The method of claim 9 further including the step of calculating the remaining minutes of charge left in the battery.

13. An apparatus for monitoring the power of a battery, comprising:
 a circuit which monitors the voltage and current from the battery;
 a circuit responsive to the monitoring circuit which determines the remaining time of charge in the battery;
 microprocessing means responsive to the determining circuit which calculates the remaining time of charge in the battery in accordance with the following:

$$B=((\Sigma XY)-(n*\bar{Y}))/((\Sigma X^2)-(n*\bar{X}))$$

$$A=\bar{Y}-(B*\bar{X})$$

and $$T=((V-A)/B)-m$$

where
 A is the intercept of voltage at time 0;

B is the slope of the voltages one time;

T is the time left to reach the voltage (V);

$\Sigma XY$ is the summation of each voltage reading (Y) multiplied by its time position (x);

m is the number of voltage values; n is the summation of all time position values;

$\Sigma X^2$ is the summation of the squares of all time position values;

$\overline{X}$ is the average of all time position values;

$\overline{Y}$ is the average of all voltage values; and display means for displaying the remaining time of charge in the battery.

14. The apparatus of claim 13 further including a batter alarm which occurs when the battery is below a predetermined level.

15. The apparatus of claim 14 further including a battery low alert which occurs when the battery charge is below a predetermined level but above the battery alarm level.

* * * * *

Disclaimer

5,764,034 - George Bowman, Vernon Hills; Grace Esche, Algonquin, both of Ill. BATTERY GAUGE FOR A BATTERY OPERATED INFUSION PUMP. Patent dated June 9, 1998. Disclaimer filed January 6, 2020, by the assignee, Baxter International Inc.

I hereby disclaim the following complete claims 1-4 and 9-12 of said patent.

*(Official Gazette, October 25, 2022)*

(12) INTER PARTES REVIEW CERTIFICATE (1180th)
United States Patent (10) Number: US 5,764,034 K1
Bowman et al. (45) Certificate Issued: May 21, 2019

(54) BATTERY GAUGE FOR A BATTERY OPERATED INFUSION PUMP

(75) Inventors: George Bowman; Grace Esche

(73) Assignee: BAXTER INTERNATIONAL INC.

Trial Numbers:

IPR2016-01460 filed Jul. 19, 2016
IPR2017-00202 filed Nov. 4, 2016

Inter Partes Review Certificate for:

Patent No.: 5,764,034
Issued: Jun. 9, 1998
Appl. No.: 08/630,359
Filed: Apr. 10, 1996

The results of IPR2016-01460 and IPR2017-00202 are reflected in this inter partes review certificate under 35 U.S.C. 318(b).

INTER PARTES REVIEW CERTIFICATE
U.S. Patent 5,764,034 K1
Trial No. IPR2016-01460
Certificate Issued May 21, 2019

AS A RESULT OF THE INTER PARTES REVIEW PROCEEDING, IT HAS BEEN DETERMINED THAT:

Claims 1-4 and 9-12 are cancelled.

\* \* \* \* \*